(12) United States Patent
Christoffel

(10) Patent No.: US 9,487,550 B2
(45) Date of Patent: Nov. 8, 2016

(54) METHOD OF ISOLATING PURIFIED RNA WITH REDUCED DNA CONTAMINATIONS

(75) Inventor: Gabriele Christoffel, Köln (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/821,159

(22) PCT Filed: Sep. 6, 2011

(86) PCT No.: PCT/EP2011/065374
§ 371 (c)(1),
(2), (4) Date: May 13, 2013

(87) PCT Pub. No.: WO2012/032034
PCT Pub. Date: Mar. 15, 2012

(65) Prior Publication Data
US 2013/0225801 A1  Aug. 29, 2013

(30) Foreign Application Priority Data
Sep. 6, 2010 (EP) .................................. 10009219

(51) Int. Cl.
C07H 21/00 (2006.01)
C07H 1/08 (2006.01)
C12N 15/10 (2006.01)
C07H 19/06 (2006.01)
C07H 19/16 (2006.01)
C07H 19/073 (2006.01)
C07H 19/167 (2006.01)
C07H 1/06 (2006.01)
C07H 19/067 (2006.01)
C07H 19/04 (2006.01)

(52) U.S. Cl.
CPC .............. *C07H 1/08* (2013.01); *C12N 15/1003* (2013.01); *C07H 1/06* (2013.01); *C07H 19/04* (2013.01); *C07H 19/06* (2013.01); *C07H 19/067* (2013.01); *C07H 19/073* (2013.01); *C07H 19/16* (2013.01); *C07H 19/167* (2013.01)

(58) Field of Classification Search
None
See application file for complete search history.

(56) References Cited

U.S. PATENT DOCUMENTS

| | | | |
|---|---|---|---|
| 4,843,155 A | 6/1989 | Chomczynski | |
| 5,346,994 A | 9/1994 | Chomczynski | |
| 5,973,137 A * | 10/1999 | Heath | 536/25.4 |
| 7,001,724 B1 * | 2/2006 | Greenfield | 435/270 |
| 2005/0009045 A1 | 1/2005 | Greenfield et al. | |
| 2005/0282202 A1 | 12/2005 | Brolaski et al. | |
| 2006/0199203 A1 | 9/2006 | Hurt | |
| 2008/0057560 A1 | 3/2008 | Chomczynski | |

FOREIGN PATENT DOCUMENTS

| | | |
|---|---|---|
| WO | 95/28409 A1 | 10/1995 |
| WO | 2006/073472 A2 | 7/2006 |

OTHER PUBLICATIONS

Haubler et al. Journal of Medical Microbiology (2003), vol. 52, pp. 295-301.*
Camacho-Villasana et al., "An Improved Method for Isolating RNA From Dehydrated and Nondehydrated Chili Pepper," *Plant Molecular Biology Reporter*, 20:407-414 (Dec. 2002).
Hurt et al., "Simultaneous Recovery of RNA and DNA from Soils and Sediments," *Applied and Environmental Microbiology*, 67(10):4495-4503 (Oct. 2001).
Junttila et al., "Optimization and comparison of different methods for RNA isolation for cDNA library construction from the reindeer lichen *Cladonia rangiferina*," *BMC Research Notes*, 2:204 (5 pages) (2009).
TRI Reagent® Solution RNA/DNA/Protein Isolation Reagent, Retrieved from the Internet: URL:http://www.ambion.com/techlib/prot/bp9738.pdf, 12 Pages (2010).

* cited by examiner

*Primary Examiner* — Patrick Lewis
(74) *Attorney, Agent, or Firm* — Seed IP Law Group LLP

(57) ABSTRACT

The present invention pertains to a method of isolating RNA from a sample comprising RNA, and DNA, comprising: a) adding an acidic denaturing composition comprising a chaotropic agent and phenol to the sample; b) adding a water-insoluble organic solvent and separating the resulting phases thereby forming a multi-phase mixture comprising an aqueous phase, optionally an interphase and an organic phase, wherein the RNA is concentrated in said aqueous phase and DNA and proteins are concentrated in said organic phase and/or in said interphase; and c) isolating said RNA from said aqueous phase, wherein at least one cationic detergent is added before separating the phases. It was found that the addition of at least one cationic detergent considerably reduces the amount of DNA in the aqueous, RNA containing phase. Therefore, the present invention allows to easily isolate pure RNA which comprises considerably less DNA contaminations.

19 Claims, 6 Drawing Sheets a)

b)

a)

b)

a)

b)

METHOD OF ISOLATING PURIFIED RNA WITH REDUCED DNA CONTAMINATIONS

The present invention pertains to a method for isolating purified RNA from samples comprising RNA and DNA, wherein the amount of DNA contaminations in the purified RNA is reduced. Furthermore, the present invention is directed to compositions and methods useful for said purpose.

The isolation of pure, intact RNA is a critical step for the analysis of gene expression in molecular biology, clinical and biotechnology applications. Many methods for achieving that goal were developed in the prior art. The most frequently used methods for RNA isolation are based on phenol extraction, precipitation by using chaotropic salt solutions and the adsorption to silica. Phenol-chloroform based methods using chaoptropic salts are for example described in U.S. Pat. No. 4,843,155 and US 2008/057560. The respective methods allow either the isolation of pure RNA, or the isolation of RNA, DNA and optionally proteins from the same sample. The principal of the respective methods is to homogenize the sample in a denaturing composition comprising phenol and a chaotropic agent. The homogenate is subjected to phase separation by adding a water-insoluble organic solvent such as chloroform. Following centrifugation, the mixture separates into an aqueous phase containing RNA and an interphase and organic phase which contain DNA and proteins. For isolating RNA, the aqueous phase is collected and the RNA is isolated therefrom, for example by precipitating the RNA by adding an alcohol to said aqueous phase.

The respective methods provide substantially pure, undegraded RNA. However, the RNA isolated according to the respective phenol-chloroform based method contains residual amounts of DNA which can be detected e.g. by reverse transcription-polymerase chain reaction assays (RT-PCR). These residual DNA contaminations can disturb the downstream application of the purified RNA. This constitutes a problem, because the contaminating DNA serves as a template for DNA polymerase, thereby potentially yielding additional amplification products and thus distorting the performance of an RNA-dependent RT-PCR. Therefore, the RNA isolated using the respective methods must be further purified to render the purified RNA DNA-free.

Therefore, there were attempts in the prior art to improve the quality of the isolated RNA by reducing the amount of DNA contaminations in the purified RNA. One common practice for removing contaminating DNA is to treat the RNA containing sample with a DNase. However, performing a respective DNase treatment has drawbacks, because it increases the costs and handling steps and DNase may comprise trace amounts of RNase, thereby exposing the RNA to the risk of degradation. Further attempts to reduce DNA contaminations include an additional DNA precipitation step from the aqueous phase. Improved approaches additionally used a nucleic acid binding solid phase and suitable binding conditions for binding DNA to said solid phase, in order to remove DNA contaminations from the RNA containing aqueous phase. However, also the respective methods have drawbacks, because they increase the costs due to the necessary use of an additional nucleic acid binding solid phase and the additional handling steps. A further approach to reduce DNA contaminations was based on lowering the pH value below 4 during the phenol extraction (please refer for example to US 2008/0057560). However, also this method does not result in a satisfying reduction of DNA contaminations in the isolated RNA.

Therefore, it is inter alia an object of the present invention to provide a method for isolating RNA from a sample comprising RNA, DNA and optionally proteins which renders pure RNA and reduces the amount of DNA contaminations in the isolated RNA.

Furthermore, it is an object of the present invention to reduce the amount of DNA in an aqueous RNA containing phase that was obtained in particular during a phenol/chloroform extraction or a similar phase producing method.

SUMMARY OF THE INVENTION

The present invention is based on the finding that the addition of at least one cationic detergent to a sample that is treated by the addition of an acidic denaturing composition comprising a chaotropic agent and phenol considerably decreases the amount of DNA in the isolated RNA. The addition of said cationic detergent surprisingly has the effect that considerably less DNA remains in the RNA containing aqueous phase that is obtained when adding a water-insoluble organic solvent such as e.g. chloroform. Without being bound by theory it is assumed that the addition of the cationic detergent has the effect that more DNA is removed from the RNA containing aqueous phase and thus, is directed to the interphase and/or the organic phase formed during phase separation. Thus, by adding the cationic detergent, the DNA is efficiently removed from the RNA containing aqueous phase and is concentrated in the resulting interphase and/or the organic phase. This considerably reduces the amount of DNA contaminations in the RNA that is subsequently isolated from said aqueous phase. Therefore, the present invention provides considerable advantages over the prior art and makes additional treatments of the aqueous RNA containing phase for removing DNA contaminations such as for example DNase treatments or the removal of DNA contaminations by the use of specific nucleic acid binding phases or additional purification steps obsolete.

According to a first aspect of the present invention, a method of isolating at least RNA from a sample comprising RNA and DNA is provided, said method comprising the following steps:
 a) adding an acidic denaturing composition comprising a chaotropic agent and phenol to the sample;
 b) adding a water-insoluble organic solvent and separating the resulting phases, thereby forming a multi-phase mixture comprising an aqueous phase, optionally an interphase and an organic phase, wherein the RNA is concentrated in said aqueous phase and DNA is concentrated in said organic phase and/or in said interphase; and
 c) isolating said RNA from said aqueous phase,
wherein at least one cationic detergent is added before finally separating the phases.

As discussed above, the addition of at least one cationic detergent before separating the individual phases has the effect that DNA contaminations are considerably reduced in the RNA containing aqueous phase, if an acidic denaturing composition comprising a chaotropic agent and phenol is used for preparing the sample.

According to a second aspect, a kit for use in a method according to the present invention is provided, comprising
 a) an acidic denaturing composition comprising a chaotropic agent and phenol;
 b) a solution for reducing DNA contaminations comprising at least one cationic detergent;
 c) optionally a nucleic acid binding solid phase and
 d) optionally washing and elution buffers.

According to a third aspect, a method is provided for reducing the amount of DNA in an RNA containing aqueous phase formed in a RNA isolation method which involves the use of an acidic denaturing composition comprising a chaotropic agent and phenol, wherein at least one cationic detergent is added to a sample homogenised in said acidic denaturing composition before the phases obtained by the addition of a water-insoluble organic solvent are separated into an aqueous phase, optionally an interphase and an organic phase.

According to a fourth aspect, the present invention pertains to the use of at least one cationic detergent for reducing the amount of DNA in an RNA containing aqueous phase which is obtained by
 homogenising a sample in an acidic denaturing composition comprising a chaotropic agent and phenol;
 adding a water-insoluble organic solvent and
 separating the mixture into an aqueous phase, optionally an interphase and an organic phase,
wherein the cationic detergent is added before finally separating the phases.

According to a fourth aspect, the present invention pertains to the use of at least one cationic detergent for increasing the amount of DNA in an optional interphase and/or an organic phase by decreasing the amount of DNA in an RNA containing aqueous phase which is obtained by
 homogenising a sample in an acidic denaturing composition comprising a chaotropic agent and phenol;
 adding a water-insoluble organic solvent and
 separating the mixture into an aqueous phase, optionally an interphase and an organic phase,
wherein the cationic detergent is added before finally separating the phases.

As discussed above, the addition of the cationic detergent before separating the phases considerably reduces the amount of DNA in the RNA containing aqueous phase when preparing the sample in an acidic denaturing composition comprising a chaotropic agent and phenol. This allows e.g. the isolation of pure RNA which comprises less DNA contaminations.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
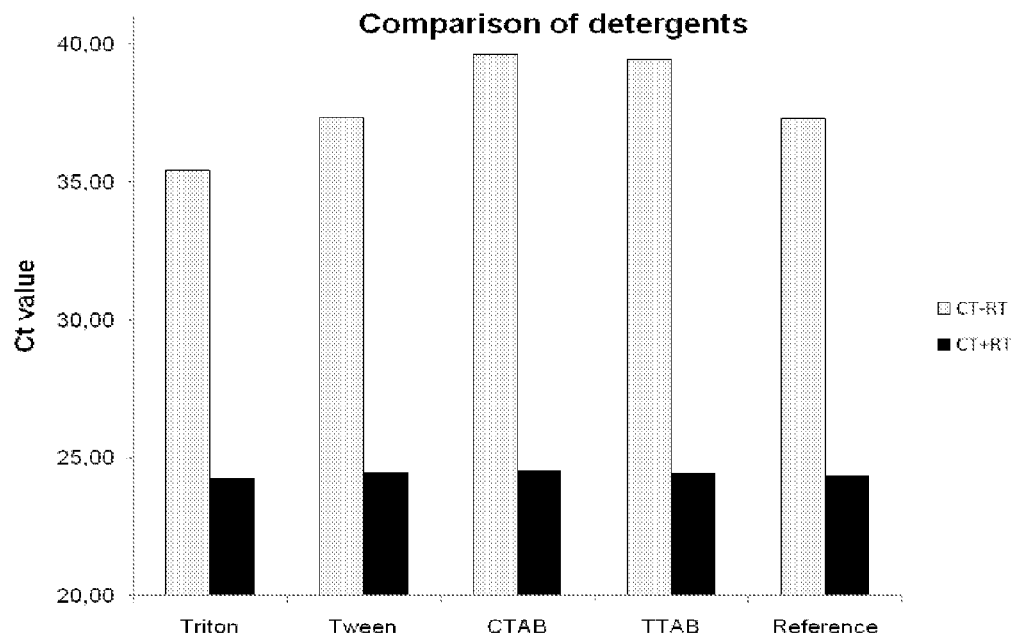
FIG. 1 shows results of qRT-PCRs carried out using the RNA isolated according to Example 1. a) Ct values, b) ΔCt values.
Figure 1:
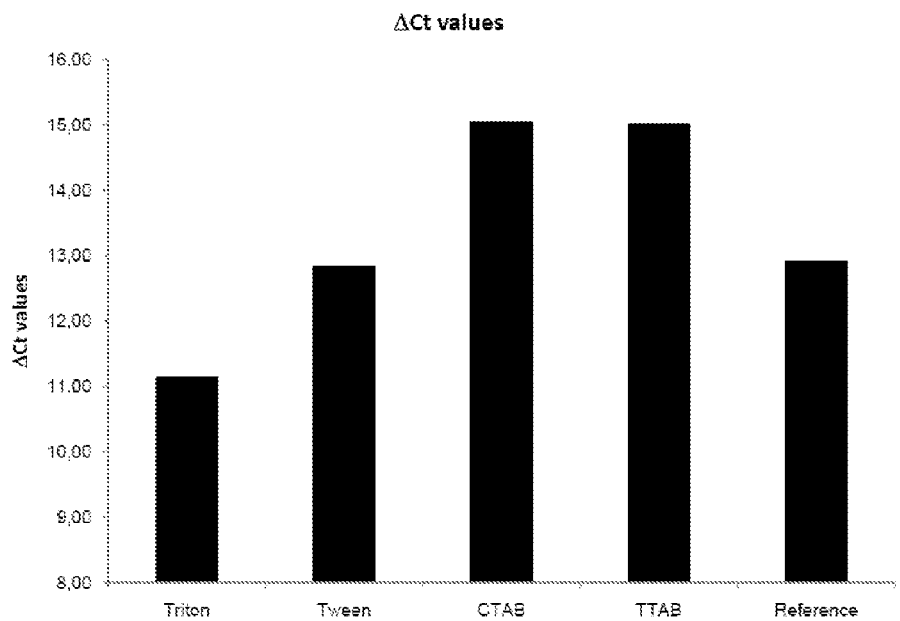

The present invention pertains to an RNA isolation method that is based on the use of phenol, a chaotropic agent and a water-insoluble organic solvent such as e.g. chloroform. In respective methods, a multi-phase mixture is formed, comprising an RNA containing aqueous phase, optionally an interphase and an organic phase. DNA and proteins (if comprised in the sample) are comprised in the interphase and/or the organic phase. The present invention is based on the finding that the amount of DNA can be considerably reduced in the RNA containing aqueous phase, if at least one cationic detergent is added before finally separating the phases. The addition of at least one cationic detergent has the effect that more DNA is removed from the RNA containing aqueous phase and accordingly, is concentrated in the interphase and/or the organic phase. Because DNA is more effectively removed from the RNA containing aqueous phase, the RNA isolated from a respectively DNA depleted aqueous phase comprises less amounts of DNA and thus, less DNA contaminations. Therefore, the present invention provides a solution to the problem of residual DNA contaminations in the purified RNA which is effective, simple and does not jeopardize the quality of the RNA. Rather, the quality of the RNA is often even improved over methods wherein no cationic detergent is added. Furthermore, the method according to the present invention is very cost-efficient, because there is no necessity to use of additional materials such as solid phases or enzymes, such as e.g. DNA binding columns or DNase. Therefore, the present invention has considerable advantages.

According to a first aspect of the present invention, a method of isolating at least RNA from a sample comprising RNA and DNA is provided, said method comprising the following steps:
a) adding an acidic denaturing composition comprising a chaotropic agent and phenol to the sample;
b) adding a water-insoluble organic solvent and separating the resulting phases, thereby forming a multi-phase mixture comprising an aqueous phase, optionally an interphase and an organic phase, wherein the RNA is concentrated in said aqueous phase, and DNA is concentrated in said organic phase and/or in said interphase; and
c) isolating said RNA from said aqueous phase,
wherein at least one cationic detergent is added before finally separating the phases.

Steps a) to c) are steps which are also performed in the methods known in the prior art for isolating RNA. In step a) the sample is processed, usually lysed and/or homogenized, in an acidic denaturing composition comprising a chaotropic agent and phenol. The resulting mixture is separated into an organic phase, usually an interphase (depending on the sample) and an aqueous phase by adding in step b) a water-insoluble organic solvent such as chloroform. The formation of said phases can be promoted by centrifugation. In step c), the RNA is isolated from the aqueous phase. The improvement of the present invention lies in that at least one cationic detergent is added to the mixture before finally separating the phases. It was surprisingly found that the addition of said cationic detergent considerably reduces the amount of DNA in the RNA containing aqueous phase, if an acidic denaturing composition comprising a chaotropic agent and phenol is used for preparing the sample. This combination of reagents used in the method according to the present invention (in particular the chaotropic agent, phenol, the cationic detergent and the water insoluble organic solvent) is important for achieving the advantages of the present invention. E.g., the advantages are not achieved when adding the chaotropic agent or the cationic detergent alone. Therefore, the precise combination as described herein is decisive. The advantages achieved with the specific combination of steps as is taught by the present invention, is evidenced by the examples provided herein.

According to one embodiment, at least one cationic detergent having the following formula is used:

YR1R2R3R4X wherein

Y is nitrogen or phosphor;

R1, R2, R3 and R4 independently are selected from a branched or unbranched C1-C20 alkyl residue, a C3 to C6 alkylene residue, a C3 to C6 alkinyl residue and/or a C6-C26 aralkyl residue and wherein preferably at least one of R1, R2, R3 or R4 is a C6 to C20 alkyl residue and even more preferred is at least a C10 alkyl residue;

X— is the anion of an anorganic or organic mono- or polybasic acid.

Examples of cationic detergents include but are not limited to quarternary ammonium salts, amines with amide linkage, polyoxyethylene alkyl and alicyclic amines, N,N,N',N' tetrakis substituted ethylenediamines, 2-alkyl 1-hydroxyethyl 2 imidazoline ethoxylated amines and alkyl ammonium salts.

According to one embodiment, a cationic detergent is used which comprises a permanently charged quaternary ammonium cation as polar head group. Preferably, the cationic detergent is an alkyltrimethylammonium salt. Preferably, the cationic detergent comprises ammonium bromide or ammonium chloride. Most preferably, the cationic detergent is selected from the group consisting of cetyl trimethyl ammonium bromide (CTAB), tetra decyl trimethyl ammonium bromide (TTAB) and dodecyl trimethyl ammonium bromide (DTRB) or the corresponding compounds comprising a chloride instead of the bromide.

Further cationic detergents include but are not limited to didecyldimethylammoniumchlorid, benzalkoniumchloride, n-dodecyl trimethyl ammonium bromide (DTAB), trimethyl-tetradecylammoniumbromid, N,N' dimethyldodecylamine-N-oxide ctenidine dihydrochloride; alkyltrimethylammonium, salts hexadecyl trimethyl ammonium bromide, cetylpyridinium chloride (CPC), polyethoxylated tallow amine (POEA), benzalkonium chloride (BAC), benzethonium chloride (BZT), 5-Bromo-5-nitro-1,3-dioxane, dimethyldioctadecylammonium chloride, dioctadecyldimethylammonium bromide (DODAB), hexadecyltrimethylammonium bromide (HTAB), cetylpyridinium chloride, dimethyl dioctadecyl ammonium bromide, cocos alkyl dimethyl benzyl ammonium chloride, cocos alkyl dimethyl benzyl ammonium chloride, alkyl hydroxyethyl dimethyl ammonium chloride, di-oleic acid triethanolamine esterquat, distearyl dimethyl ammonium chloride, ditallow acid triethanolamine esterquat, triethanolamine esterquat.

According to one embodiment, the at least one cationic detergent is added in a concentration which renders a cationic detergent concentration in the homogenised sample of step a) and/or in the mixture obtained after the addition of the water-insoluble organic solvent in step b), which is selected from the group consisting of 0.01% to 10%, 0.03% to 7.5%, 0.03% to 5%, 0.04% to 2.5%, 0.04% to 2% and 0.03% to 1.7% based on the total volume. Preferably, the cationic detergent or the mixture of cationic detergents is comprised in a concentration selected from the group consisting of at least 0.03%, at least 0.04%, at least 0.05%, at least 0.06%, at least 0.08%, at least 0.09%, at least 0.1% and at least 0.15%. As discussed above, also mixtures of cationic detergents, preferably CTAB mixed with TTAB, can be used.

According to a preferred embodiment, the at least one cationic detergent is added in form of a solution. In said solution, the cationic detergent is preferably comprised in a concentration selected from the group consisting of 0.1% to 20%, 0.5% to 10%, 0.1% to 5%, 0.5% to 5%, 0.1% to 3%, 0.5% to 3%, and most preferably in a concentration of 0.1% to 1% and 0.5% to 1%, based on the total volume of the solution. The same applies in case a mixture of cationic detergents is used.

Said solution comprising the at least one cationic detergent may comprise additional ingredients such as e.g. salts. The salt which is preferably comprised in said solution may be selected from the group consisting of alkaline metal salts, e.g. sodium chloride, lithium chloride, potassium chloride, ammonium chloride, sodium acetate, sodium nitrate, ammonium sulphate, sodium sulphate, lithium sulphate, potassium sulfate and mixtures thereof. The addition of a respective salt in particular has the advantage that the cationic detergent remains in solution. Preferably, said salt is comprised in the solution in a concentration selected from the group consisting of 0-10M, preferably 0.5 to 5M, more preferred 0.5 to 1.5M.

There are several options how the cationic detergent can be added before separating the phases. According to one embodiment, the cationic detergent is added during step a) either before, during or after the acidic denaturing composition is, respectively, was added to the sample. The cationic detergent may also be comprised in the acidic denaturing composition. Furthermore, the cationic detergent may be added together with, respectively at the same time when the water-insoluble organic solvent is added in step b). However, it is important that the cationic detergent is added before the final phase separation is performed in order to allow the cationic detergent to exert its beneficial effects with respect to reducing the amount of DNA in the aqueous RNA containing phase. As the final phase separation is decisive, it is also within the scope of the present invention to perform an initial phase separation, then adding the cationic detergent to the aqueous phase and then finally separating the phases, e.g. supported by centrifugation, in order to allow that the cationic detergent and the residual DNA is removed from the aqueous phase into the organic and/or the interphase. However, in particular to spare handling steps it is preferred that the cationic agent is added before or at the same time the water-insoluble organic solvent is added. According to a preferred embodiment, the cationic detergent is added separately and thus after the sample was mixed with the acidic denaturing composition and before the water-insoluble organic solvent is added. As is shown in the examples, particularly good results are achieved when adding the at least one cationic detergent after step a) and before step b).

The phase separation can be achieved by sedimentation. According to one embodiment, the multi-phase is mixture is formed by centrifuging the sample. Here, it is preferred to centrifuge the sample at lower temperatures and thus temperatures below room temperature. Preferably, the temperature is ≤15° C., ≤10° C. and particularly preferred are even lower temperatures such as ≤7° C., ≤5° C. and ≤4° C. It was found, that centrifugation at lower temperature assists the phase separation and furthermore, promotes the reduction of DNA in the RNA containing aqueous phase when using a cationic detergent.

For isolating the RNA from said aqueous phase, basically any method known in the prior art for isolating RNA from an aqueous solution can be used. Preferably, the RNA is isolated by adding at least one alcohol to said aqueous phase, thereby precipitating the RNA. According to one embodiment, the respectively precipitated RNA can be recovered by centrifugation of the aqueous phase and decanting the supernatant liquid.

Preferably, the aqueous phase is mixed with at least one alcohol and said mixture is then contacted with a nucleic acid binding solid phase in order to assist the nucleic acid purification.

As nucleic acid binding solid phase, any material that is capable of binding nucleic acids can be used and thus includes a variety of materials that are capable of binding nucleic acids under suitable conditions. Exemplary solid phases that can be used in conjunction with the present invention include, but are not limited to, compounds comprising silica and siliceous solid phases, including but not limited to, silica particles, silicon dioxide, diatomaceous earth, glass, alkylsilica, aluminum silicate, and borosilicate; nitrocellulose; diazotized paper; hydroxyapatite (also referred to as hydroxyl apatite); nylon; metal oxides; zirconia; alumina; polymeric supports, diethylaminoethyl- and triethylaminoethyl-derivatized supports, hydrophobic chromatography resins (such as phenyl- or octyl Sepharose) and the like. The term solid phase is not intended to imply any limitation regarding its form or design. Thus, the term solid phase encompasses appropriate materials that are porous or non-porous; permeable or impermeable; including but not limited to membranes, filters, sheets, particles, magnetic particles, beads, gels, powders, fibers, and the like. According to one embodiment, the surface of the solid phase is not modified and is, e.g., not modified with functional groups. Preferably, a nucleic acid binding membrane is used. Suitable membranes include but are not limited to hydrophilic membranes, hydrophobic membranes and membranes which bind nucleic acids via ion exchange. Examples include but are not limited to silica membranes and other membranes comprising silica, nylon membranes, cellulose membranes such as nitrocellulose membranes. Preferably, the membrane is porous. Furthermore, it is preferred to use a membrane comprising or consisting of silica.

As alcohol, it is preferred to use short chained branched or unbranched alcohols with preferably one to 5 carbon atoms. Examples are methanol, ethanol, propanol, isopropanol and butanol. Also mixtures of alcohols can be used. The alcohol is preferably selected from isopropanol and ethanol because said alcohols are in particular effective to precipitate RNA.

The concentration of alcohol used for isolating the RNA depends on whether it is intended to include small RNAs in the isolated total RNA or not. In case it is intended to also purify small RNAs such as miRNAs, it is recommended to use higher alcohol concentrations. In case it is not desired to include respective small RNA species in the isolated total RNA, lower alcohol concentrations are preferred. The concentration of alcohol when mixed with the aqueous phase may lie in a range of 10% v/v to 90% v/v in the resulting mixture. For isolating total RNA including small RNA, it is beneficial to use an alcohol concentration of ≥40% v/v, preferably ≥50% v/v. In case it is not desired to include small RNAs, the concentration of alcohol is preferably ≤40% v/v. Thus, the concentration may be selected from the group consisting of at least 20%, at least 30% v/v, at least 40% v/v, at least 50% v/v and at least 60% v/v when mixed with the aqueous phase. Preferably, the alcohol concentration lies in a range of 20% v/v to 90% v/v/ or 30% v/v to 85%, preferably in the range of 30% v/v to 70% v/v when mixed with the aqueous phase.

The term "sample" is used herein in a broad sense and is intended to include a variety of sources that contain nucleic acids. The sample may be a biological sample but the term also includes other, e.g. artificial samples which comprise nucleic acids. Exemplary samples include, but are not limited to, whole blood; blood products; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; tissues, including but not limited to, liver, spleen, kidney, lung, intestine, brain, heart, muscle, pancreas; cell cultures, as well as lysates, extracts, or materials obtained from the samples described above or any cells and microorganisms and viruses that may be present on or in a sample and the like. Materials obtained from clinical or forensic settings that contain nucleic acids are also within the intended meaning of the term "sample". Furthermore, the skilled artisan will appreciate that lysates, extracts, or processed materials or portions obtained from any of the above exemplary samples are also within the scope of the term "sample". Preferably, the sample is a biological sample derived from a human, animal, plant, bacteria or fungi. Preferably, the sample is selected from the group consisting of cells, tissue, bacteria, virus and body fluids such as for example blood, blood products such as buffy coat, plasma and serum, urine, liquor, sputum, stool, CSF and sperm, epithelial swabs, biopsies, bone marrow samples and tissue samples, preferably organ tissue samples such as lung, kidney or liver. The method according to the present invention is particularly suitable for isolating RNA from tissue samples, in particular organ tissue samples. According to one embodiment, the tissue is not blood. According to one embodiment, the sample is no bacterial sample or a sample derived from bacteria.

The terms "small nucleic acid" and "small nucleic acids" in particular refer to nucleic acids having a length of less than 1000 nt, 500 nt, 400 nt, 300 nt, 100 nt or less than 70 nt and include but are not limited to miRNA, siRNA and other short interfering nucleic acids, snoRNAs, snRNAs, tRNA, hnRNA, circulating nucleic acids, fragments of genomic DNA or RNA, degraded nucleic acids, ribozymes, viral RNA or DNA, nucleic acids of infectious origin, amplification products, modified nucleic acids, plasmidical or organellar nucleic acids, artificial nucleic acids such as oligonucleotides.

The acidic denaturing composition comprising a chaotropic agent and phenol may have a composition as is described in the prior art, e.g. in U.S. Pat. No. 4,843,155 or U.S. Pat. No. 5,346,994.

Any chaotropic agent can be used in the acidic denaturing composition that causes disorder in a protein or nucleic acid by, for example, but not limited to altering the secondary, tertiary or quaternary structure of a protein or a nucleic acid while leaving the primary structure intact. Preferably, the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluoroacetate and urea. Preferably, a chaotropic salt is used. In particular, guanidinium hydrochloride and/or guanidinium thiocyanate can be used as chaotropic agent.

The chaotropic agent can be comprised in the acidic denaturing composition in a concentration selected from the group consisting of 0.1 up to the saturation limit, 0.1 to 6M, 0.5 to 4M, 0.5 to 3M and 0.5 to 2M.

Phenol is preferably comprised in the acidic denaturing composition in a concentration selected from the group consisting of 10% v/v to 70% v/v, 20% v/v to 60% v/v and 30% v/v to 50% v/v based on the total volume of the acidic denaturing composition. Preferably, the concentration of phenol lies in the range of 35% v/v to 40% v/v.

The pH value of the denaturing composition is acidic and may be ≤6, preferably ≤5. Preferably, the pH value of the acidic denaturing composition lies in the range of 3 and 6, and more preferred, in a range of 4 to 5.

Furthermore, the acidic denaturing composition may comprise a buffer in an amount sufficient to maintain said composition at an acidic pH. Said buffer may be a salt of at least one of acetate, citrate, phosphate, phthalate, tartrate or lactate and can be e.g. selected from sodium phosphate, sodium acetate and sodium citrate. Preferably, sodium acetate is used.

The acidic denaturing composition may comprise a solubilizer for maintaining the phenol in solution, especially at 4° C., and to achieve or maintain the solvent as a monophase solution. A suitable solubilizer is glycerol. According to one embodiment, the solubilizer is comprised in a concentration of about 2 to 10%, preferably about 5%.

Furthermore, the acidic denaturing composition may comprise a thiocyanate component, preferably ammonium thiocyanate or sodium thiocyanate. This additional thiocyanate component is believed to enhance the extraction of RNA from the biological sample. The thiocyanate component may be comprised in a concentration of 0.1 to 1M, preferably 0.4M.

According to one embodiment, the acidic denaturing composition has the following characteristics:
  it comprises phenol in a concentration above 30%, preferably above 35% and most preferred between 35% and 40%;
  it has a pH of 4.3 to 6, preferably 4.5 to 5;
  it comprises a chaotropic salt in a concentration of 0.5 to 4M, preferably 0.5 to 3M; and
  it preferably comprises at least one further agent selected from the group consisting of a buffer, a solubilizer and a thiocyanate compound; preferred examples and concentrations are described above.

Preferably, the acidic denaturing composition combines all of the preferred characteristics described above.

Suitable water-insoluble organic solvent include, but are not limited to caprolactone, ethylene glycol diacetate, polyethylene glycol dibenzoate, chloroform, carbon tetrachloride, bromochloropropane, bromonaphtalene, bromoanisole, cyclohexylbromide, dibromopropane, dichlorobenzoic acid or mixtures thereof. Preferably, the water-insoluble organic solvent is chloroform.

The method according to the present invention may also comprise one or more additional steps, some non-limiting options are subsequently described.

If desired, proteins (if contained in the sample) and/or the DNA can be also recovered from the organic phase and/or the interphase with the method according to the present invention. E.g. proteins can be precipitated by the addition of a lower alcohol to the organic phase and recovering the proteins by sedimentation. The DNA can be recovered from the interphase and/or the organic phase e.g. by washing with a predetermined amount of the solvent solution, sedimentation of the DNA and removal of any phenol and salt contamination from the DNA. Suitable methods for isolating DNA and/or proteins from the interphase and/or the organic phase are known in the prior art and thus, need no further description here. Performing the methods according to the present invention also has with respect to the DNA isolation the advantageous effect that the yield of DNA is increased because DNA is more efficiently removed from the aqueous phase and thus concentrated in the interphase and/or organic phase, wherefrom the DNA can be isolated.

Furthermore, one or more washing steps can be performed when isolating the RNA from the aqueous phase. Preferably, said washing steps are performed while the RNA bound to the nucleic acid binding solid phase in case a solid phase is used. For this purpose common washing solutions may be used. It is recommended to use washing solutions which do not result in a release of the RNA from the nucleic acid binding solid phase. Furthermore, the RNA containing pellet can be washed in case no binding phase is used. According to one embodiment, the solution used for washing comprises at least one chaotropic agent, at least one alcohol, at least one detergent and/or at least one buffering component. Chaotropic agents that can be used in the washing solutions include but are not limited to guanidinium hydrochloride, guanidinium thiocyanate, guanidinium isothiocyanate and sodium iodide. Furthermore, chaotropic salts can be used which comprise a chaotropic anion selected form the group consisting of trichloroacetate, perchlorate and trifluoroacetate. Examples of respective chaotropic salts are alkali salts like sodium perchlorate, sodium trichloroacetate and sodium trifluoroacetate. As alcohol for washing, short chained branched or unbranched alcohols with preferably one to 5 carbon atoms can be used for washing, respectively in the washing solution. Examples are methanol, ethanol, propanol, isopropanol and butanol. Preferably, isopropanol and/or ethanol are used. Preferably, the washing solution comprises at least 10% alcohol and at least 900 mM chaotropic salt, preferably at least 2M chaotropic salt. Furthermore, the washing solution may comprise a detergent.

Also provided is a kit suitable for use in the method according to the present invention. Said kit comprises
  a) an acidic denaturing composition comprising a chaotropic agent and phenol;

b) a solution for reducing DNA in the aqueous phase comprising at least one cationic detergent and a preferably a salt;
c) optionally a nucleic acid binding solid phase and
d) optionally washing and elution buffers.

The acidic denaturing composition preferably has the characteristics described above. It is referred to the above disclosure. Furthermore, also the solution for reducing DNA preferably has the characteristics described above. It is again referred to the above disclosure.

According to a further aspect of the present invention a method is provided for reducing the amount of DNA in an RNA containing aqueous phase formed in a RNA isolation method which involves the use of an acidic denaturing composition comprising a chaotropic agent and phenol, wherein at least one cationic detergent is added to a sample homogenised in said acidic denaturing composition before the phases obtained by the addition of a water-insoluble organic solvent are separated into an aqueous phase, optionally an interphase and an organic phase.

The present invention also pertains to the use of at least one ionic detergent for reducing the amount of DNA in an RNA containing aqueous phase which is obtained by
homogenising a sample in an acidic denaturing composition comprising a chaotropic agent and phenol;
adding a water-insoluble organic solvent and
separating the mixture into an aqueous phase, optionally an interphase and an organic phase,
wherein the ionic detergent is added before finally separating the phases. As ionic detergent, anionic detergents such as SDS and preferably, cationic detergents are used. As discussed above, the detergent is preferably a cationic detergent because a cationic detergent provides the best results with respect to reducing the amount of DNA in an RNA containing aqueous solution. Further details with respect to the acidic denaturing composition, the detergents and further details of the described use are discussed above in conjunction with the method according of the present invention. It is referred to the above disclosure. Preferably, the acidic denaturing composition combines all of the preferred characteristics described above.

The present invention also pertains to the use of at least one cationic detergent for increasing the amount of DNA in an interphase and/or an organic phase by decreasing the amount of DNA in an RNA containing aqueous phase obtained by
homogenising a sample in an acidic denaturing composition comprising a chaotropic agent and phenol;
adding a water-insoluble organic solvent and
separating the mixture into an aqueous phase, optionally an interphase and an organic phase,
wherein the cationic detergent is added before finally separating the phases.

Details with respect to the acidic denaturing composition and the cationic detergent and the associated advantages are described in detail above. It is referred to the respective disclosure which also applies here.

EXAMPLES

Example 1

Effect of different detergents on the elimination of genomic DNA during isolation of RNA from rat liver was assessed by the following method:
1. 270 mg of RNAlater-stabilized liver tissue were homogenized in 27 ml of Qiazol reagent, an acidic phenol and chaotropic salt-containing reagent, using a TissueRuptor homogenizer.
2. 1000 µl of the resulting homogenate was aliquoted into 2 ml Eppendorf tubes. Thus, 10 mg of tissue was used per sample.
3. 8 µl (5 µg) of genomic DNA was added to the Qiazol reagent prior to phase separation.
4. In a next step, 100 µl of the following detergents were added to the homogenates (in duplicate):
Triton X-100 [100%]
Tween20 [20%]
Cetyl-trimethyl-ammonium bromide [1%], CTAB
Tetra-decyl-trimethyl-ammonium bromide [1%], TTAB.
For the reference, no detergent was added ("reference").
This was followed by the addition of 200 µl chloroform and vortexing.
5. The samples were centrifuged for 15 min at 12.000×g at 4° C. and the resulting aqueous phase was transferred into new Eppendorf tubes.
6. 1.5 volumes of absolute ethanol were added to the each aqueous phase and mixed.
7. The mixture was transferred onto RNeasy mini columns (Qiagen) and centrifuged for 15 s at 8.200×g, followed by a wash with 700 µl RVVT buffer (Qiagen) and subsequent centrifugation, 15 s at 8.200×g.
8. The columns were washed twice with 500 µl RPE buffer (Qiagen) centrifuged at 8.200×g for 15 s and 2 minutes respectively, followed by a final centrifugation step at maximum speed for 1 minute.
9. Bound RNA was eluted into 30 µl RNase-free water by centrifugation at 8.200×g for 1 min and the RNA concentration was determined spectroscopically using a NanoDrop (ThermoScientific). The results are shown in Table 1.

TABLE 1

Quantification of isolated RNA using Triton X-100, Tween20, CTAB or TTAB as detergents. Nucleic acid quantification was done using a NanoDrop spectrometer (ThermoScientific).

| detergent | A260 | A280 | 260/280 | 260/230 | ng/µl | RNA yield [µg] | Mean |
|---|---|---|---|---|---|---|---|
| Blank | −0.008 | −0.024 | 0.33 | 3.10 | −0.32 | | |
| Triton x-100 | 35.705 | 17.434 | 2.05 | 1.95 | 1428.2 | 42.85 | 37.71 |
| Triton x-100 | 27.149 | 13.336 | 2.04 | 1.96 | 1085.95 | 32.58 | |
| Tween20 | 31.686 | 15.717 | 2.02 | 1.96 | 1267.46 | 38.02 | 36.14 |
| Tween20 | 28.553 | 14.056 | 2.03 | 1.98 | 1142.1 | 34.26 | |
| CTAB | 26.687 | 13.115 | 2.03 | 1.97 | 1067.46 | 32.02 | 32.24 |
| CTAB | 27.039 | 13.182 | 2.05 | 1.97 | 1081.56 | 32.45 | |
| TTAB | 27.278 | 13.353 | 2.04 | 1.98 | 1091.11 | 32.73 | 34.49 |
| TTAB | 30.206 | 14.758 | 2.05 | 1.98 | 1208.25 | 36.25 | |
| reference | 29.524 | 14.469 | 2.04 | 1.93 | 1180.97 | 35.43 | 32.23 |
| reference | 24.184 | 11.942 | 2.03 | 1.82 | 967.37 | 29.02 | |

As can be seen, all protocol variants result in a good RNA yield. However, the used spectrometric methods do not strictly differentiate between RNA and DNA and thus, RNA as well as DNA is determined in the "RNA yield". The yield of pure RNA is improved when using the method according to the present invention compared to the reference method and the methods which use the non-cationic detergents Triton and Tween, because the amount of DNA in the isolated RNA is considerably decreased when using the method according to the present invention as is subsequently demonstrated by Table 3 and corresponding FIG. 1.

10. RNA integrity was assessed using an Agilent BioAnalyzer 2100® to compare the influence of the tested detergents on RNA integrity. The results are shown in Table 2.

TABLE 2

Higher RIN (RNA integrity number) values indicate a higher degree of RNA integrity. RIN values range between 10 (intact RNA) and 1 (totally degraded RNA).

| detergent | Triton | Tween | CTAB | TTAB | Ref. |
|---|---|---|---|---|---|
| RNA Area | 1207.1 | 1105 | 810.8 | 793.2 | 891.3 |
| RNA Conc. | 520 ng/µl | 476 ng/µl | 349 ng/µl | 342 ng/µl | 384 ng/µl |
| Ratio [28 s/18 s] | 1.2 | 1.4 | 1.4 | 1.4 | 1.4 |
| RIN | 8.0 | 8.30 | 8.90 | 8.90 | 8.60 |

Table 2 shows that the highest RIN numbers are obtained with the method according to the present invention. Thus, the RNA integrity of the RNA isolated with the method according to the present invention is better than the RNA integrity of the RNA that was isolated using the reference method or when adding other non-cationic detergents.

11. The RNA samples were diluted 1:50 with RNAse-free water and then reverse transcribed with 10 pmole of gene-specific primers and probe (PGK1 primer mix, PGK1 probe) each using a QuantiTect RT-PCR kit (Qiagen) with and without reverse transcriptase in a reaction volume of 25 µl:
  (1) 30 min@50° C.
  (2) 15 min@95° C.
  (3) 15 s@95° C.
  (4) 1 min@60° C., repeat steps (3), (4) for 40 cycles.
The resulting Ct and ΔCt values are shown in Table 3 and FIGS. 1 a) (Ct values) and 1b) (ΔCt values).

TABLE 3

Results of qRT-PCRs carried out using the RNA isolated from example 1. "−RT" denotes control reactions, which did not contain reverse transcriptase, "+RT" denotes qRT-PCR reactions with reverse transcriptase.

|  | Ct − RT | Ct + RT | ΔCt |
|---|---|---|---|
| Triton | 35.42 | 24.27 | 11.15 |
| Tween | 37.31 | 24.47 | 12.84 |
| CTAB | 39.61 | 24.55 | 15.06 |
| TTAB | 39.45 | 24.42 | 15.03 |
| Ref. | 37.29 | 24.36 | 12.93 |

In the "−RT" reactions, only the DNA contaminations can serve as template and accordingly, are amplified in the PCR (the RNA is not reverse transcribed in the "−RT" reactions and thus, can not serve as template). Therefore, in samples comprising low amounts of DNA, the threshold is reached after more cycles and accordingly, the Ct values are higher. Thus, the higher the Ct value in the "−RT" reaction, the lower the amount of template and thus, the lower the amount of DNA contaminations in the isolated RNA. The highest Ct values are achieved with the method according to the present invention. In order to ensure, that the higher Ct values are not attributable to a lower overall yield of nucleic acids, the Ct values for the "+RT" reaction were determined, wherein the RNA is reverse transcribed and accordingly, can serve as template for the PCR. The Ct values are lower in all "+RT" reactions, because therein, the reverse transcribed RNA (and the DNA contaminations) can serve as template for the PCR and thus, the threshold is reached earlier as in the "−RT" reactions. As can be seen from the results, the obtained Ct values are approximately equal in all tested samples.

The ΔCt values (ΔCt=(Ct of the "−RT" reaction)−(Ct of the "+RT" reaction)) show the differences between the two reactions and thus, indicate the amount of DNA contaminations in the isolated RNA. The higher the ΔCt value, the lower the amount of DNA contamination in the isolated RNA. Table 3 and FIGS. 1 a) and b) demonstrate, that the RNA isolated according to the present invention wherein cationic detergents were added comprises considerably less amounts of DNA contaminations than the reference method. Thus, DNA contaminations are effectively reduced by the teachings of the present invention. The other, non-cationic detergents were not able to reduce the amount of DNA contaminations. Conversely, they even lead to an increase of DNA in the isolated RNA, as can be seen from the ΔCt values that are even lower than the ΔCt value of the reference method.

Example 2

The following experiment was done to assess the amount of genomic DNA co-purified during RNA isolation from different tissues using the Qiazol reagent while adding the detergent directly to the homogenate:
  1. 200 mg of RNAlater-stabilized lung, kidney, heart, spleen and brain tissue were homogenized in 8 ml Qiazol reagent, using a TissueRuptor homogenizer.
  2. Homogenates, 1000 µl each (corresponding to 25 mg tissue per sample), were aliquoted into 2 ml Eppendorf tubes and 100 µl of the following detergent stock solutions were added thereto:
    Cetyl-trimethylammonium bromide [1%], CTAB
    Tetra-decyltrimethylammonium bromide [1%], TTAB.
    For the reference, no detergent was added ("reference").
    This was followed by the addition of 200 µl chloroform and vortexing.
  3. The samples were centrifuged for 15 min at 12.000×g at 4° C. and the resulting aqueous phase was transferred into new Eppendorf tubes.
  4. The supernatant was mixed with 1.5 volumes of absolute ethanol and the aqueous phases was transferred onto RNeasy mini columns (Qiagen) and centrifuged for 15 s at 8.200×g, followed by a wash with 700 µl RWT buffer (Qiagen) and subsequent centrifugation, 15 s at 8.200×g.
  5. The columns were then washed twice with 500 µl RPE buffer (Qiagen) at 8.200×g for 15 s and 2 minutes respectively, followed by a final centrifugation step at maximum speed for 1 minute.
  6. Bound RNA was eluted into 30 µl RNase-free water by centrifugation at 8.200×g for 1 min and the RNA concentration was determined spectroscopically using a NanoDrop (ThermoScientific). The results are shown in Table 4.

TABLE 4

Quantification of RNA isolated from RNAlater-stabilized tissues using no detergent ("—"), [1%] ("CTAB") or [1%] ("TTAB"). RNA quantification was done using a NanoDrop (ThermoScientific).

| Tissue | Detergent | A260 | A280 | 260/280 | 260/230 | ng/µl | RNA yield [µg] | Mean |
|---|---|---|---|---|---|---|---|---|
| Lung | — | 46.489 | 22.449 | 2.07 | 2.14 | 1860.0 | 55.80 | 49.89 |
|  |  | 36.654 | 17.840 | 2.05 | 2.10 | 1466.0 | 43.98 |  |
| Lung | CTAB | 28.391 | 13.337 | 2.13 | 2.10 | 1136.0 | 34.08 | 34.22 |
|  |  | 28.615 | 13.288 | 2.15 | 2.12 | 1145.0 | 34.35 |  |
| Lung | TTAB | 32.779 | 15.829 | 2.07 | 2.12 | 1311.0 | 39.33 | 39.50 |
|  |  | 33.057 | 15.950 | 2.07 | 2.12 | 1322.0 | 39.66 |  |
| Kidney | — | 67.937 | 33.207 | 2.05 | 2.15 | 2717.0 | 81.51 | 80.39 |
|  |  | 66.060 | 32.092 | 2.06 | 2.13 | 2642.0 | 79.26 |  |
| Kidney | CTAB | 61.260 | 30.006 | 2.04 | 2.03 | 2450.0 | 73.50 | 70.53 |
|  |  | 56.288 | 27.522 | 2.05 | 2.09 | 2252.0 | 67.56 |  |
| Kidney | TTAB | 83.496 | 41.914 | 1.99 | 2.03 | 3340.0 | 100.20 | 94.16 |
|  |  | 73.435 | 36.589 | 2.01 | 2.08 | 2937.0 | 88.11 |  |
| Heart | — | 39.950 | 19.412 | 2.06 | 2.16 | 1598.0 | 47.94 | 41.63 |
|  |  | 29.422 | 14.065 | 2.09 | 2.18 | 1177.0 | 35.31 |  |
| Heart | CTAB | 23.998 | 11.216 | 2.14 | 2.22 | 959.9 | 28.80 | 28.47 |
|  |  | 23.445 | 11.083 | 2.12 | 2.22 | 937.8 | 28.13 |  |
| Heart | TTAB | 30.764 | 14.469 | 2.13 | 2.05 | 1231.0 | 36.93 | 34.97 |
|  |  | 27.505 | 13.121 | 2.10 | 2.15 | 1100.0 | 33.00 |  |
| Spleen | — | 67.898 | 33.537 | 2.02 | 1.99 | 2716.0 | 81.48 | 80.78 |
|  |  | 66.713 | 32.764 | 2.04 | 2.02 | 2669.0 | 80.07 |  |
| Spleen | CTAB | 65.670 | 33.013 | 1.99 | 2.03 | 2627.0 | 78.81 | 69.66 |
|  |  | 50.415 | 24.906 | 2.02 | 2.04 | 2017.0 | 60.51 |  |
| Spleen | TTAB | 63.087 | 30.851 | 2.04 | 2.03 | 2523.0 | 75.69 | 72.21 |
|  |  | 57.286 | 27.859 | 2.06 | 2.02 | 2291.0 | 68.73 |  |
| Brain | — | 23.881 | 11.279 | 2.12 | 2.15 | 955.2 | 28.66 | 30.11 |
|  |  | 26.289 | 12.786 | 2.06 | 2.16 | 1052.0 | 31.56 |  |
| Brain | CTAB | 24.501 | 11.645 | 2.10 | 2.11 | 980.0 | 29.40 | 29.81 |
|  |  | 25.168 | 11.965 | 2.10 | 2.03 | 1007.0 | 30.21 |  |
| Brain | TTAB | 22.299 | 10.787 | 2.07 | 2.14 | 892.0 | 26.76 | 26.92 |
|  |  | 22.572 | 10.757 | 2.10 | 2.16 | 902.9 | 27.09 |  |

As can be seen, the yield was good with all protocols but the RNA isolated with the method according to the present invention comprises much less DNA and therefore, the yield of pure RNA was often even increased as is also demonstrated subsequently by Table 6.

7. RNA integrity was assessed using an Agilent BioAnalyzer 2100, the results are shown in Table 5.

As before, the RIN is either equal to the reference method or even better when using the method according to the present invention.

8. RNA samples were diluted with RNase-free water as follows: lung 1:80, kidney 1:100, heart 1:50, spleen 1:100, brain 1:50. 2 µl of each dilution were reverse transcribed with 10 pmole gene-specific primers and

TABLE 5

Assessment of RNA integrity, which was isolated in example 2 using an Agilent BioAnalyzer 2100.

| | detergent | | | | | |
|---|---|---|---|---|---|---|
| Tissue | — lung | CTAB lung | TTAB lung | — kidney | CTAB kidney | TTAB kidney |
| RNA Area | 178.6 | 143 | 165.3 | 435.3 | 331.5 | 347.8 |
| RNA Conc. | 93 ng/µl | 74 ng/µl | 86 ng/µl | 226 ng/µl | 172 ng/µl | 180 ng/µl |
| Ratio [28 s/18 s] | 1.6 | 1.5 | 1.5 | 1.4 | 1.4 | 1.5 |
| RIN | 9.40 | 9.60 | 9.80 | 9.10 | 9.10 | 9.0 |

Figure 2:
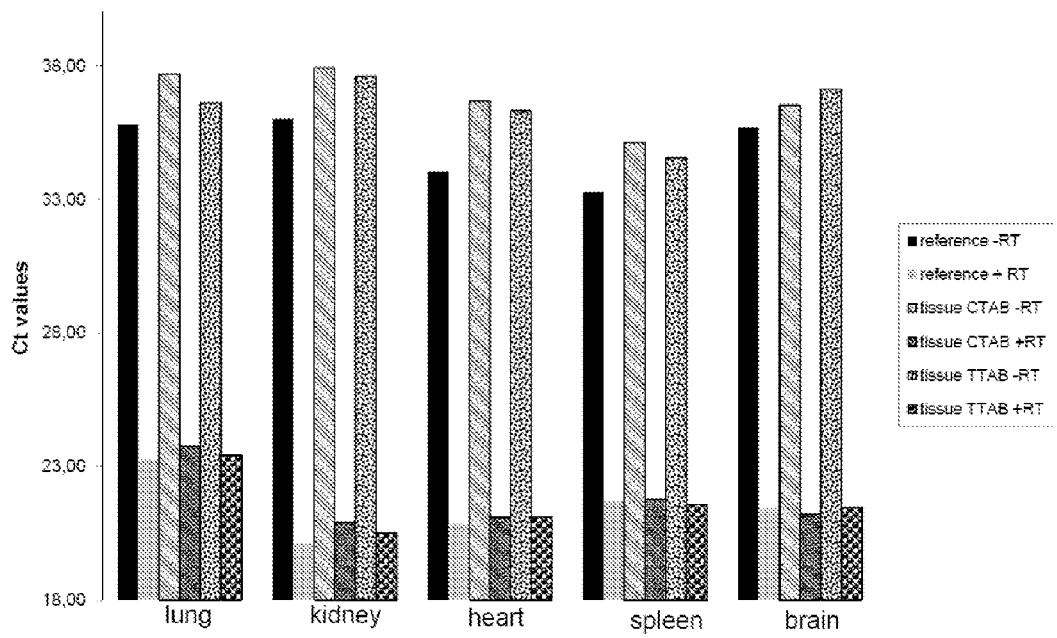
FIG. 2 shows quantification of genomic DNA co-purification by qRT-PCR using the "QuantiTect RT-PCR" kit (Qiagen) with gene-specific primers PGK1 primer mix, and PGK1 probe measured according to Example 2. a) Ct values, b) ΔCt values.
Figure 2:
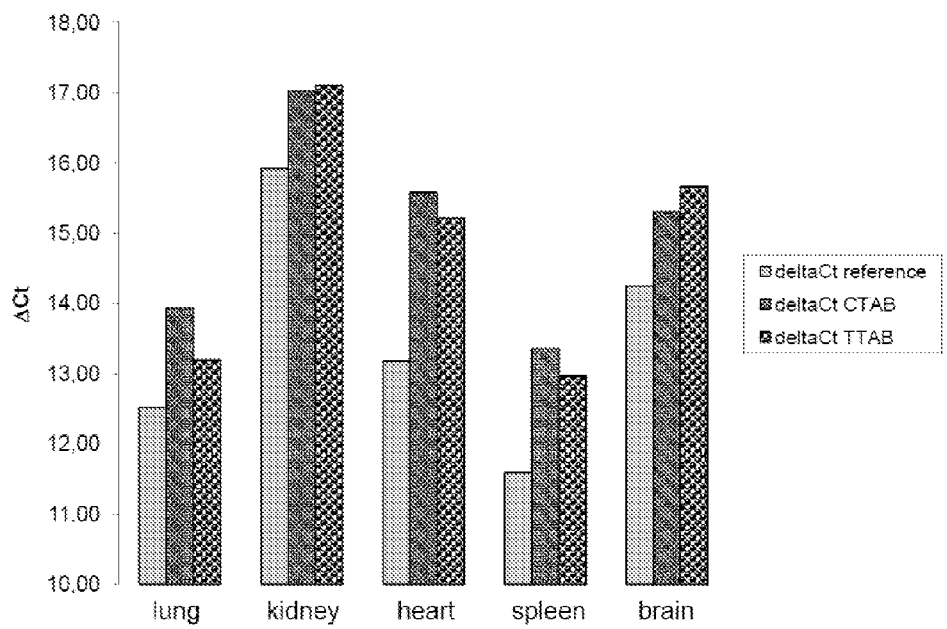

| | Detergent | | | | | |
|---|---|---|---|---|---|---|
| Tissue | — heart | CTAB heart | TTAB heart | — spleen | CTAB spleen | TTAB spleen |
| RNA Area | 163.4 | 138.7 | 121.9 | 403.8 | 444.4 | 435.2 |
| RNA Conc. | 85 ng/µl | 72 ng/µl | 63 ng/µl | 209 ng/µl | 230 ng/µl | 226 ng/µl |
| Ratio [28 s/18 s] | 1.4 | 1.5 | 1.5 | 1.3 | 1.5 | 1.6 |
| RIN | 8.70 | 8.70 | 8.60 | 7.0 | 7.90 | 7.90 | probe (PGK1 primer mix, PGK1 probe) using a QuantiTect RT-PCR kit (Qiagen) with and without reverse transcriptase in a reaction volume of 25 μl:
(1) 30 min @50° C.
(2) 15 min @95° C.
(3) 15 s @95° C.
(4) 1 min @60° C., repeat steps (3), (4) for 40 cycles.
The resulting Ct and ΔCt values are shown in Table 6 and corresponding FIGS. 2 *a*) and 2 *b*).

TABLE 6

Quantification of genomic DNA co-purification by qRT-PCR using the "QuantiTect RT-PCR" kit (Qiagen) with gene-specific primers PGK1 primer mix, PGK1 probe. "−RT" indicates reactions without reverse transcriptase, "+RT" reactions with reverse transcriptase.

|        | Ct − RT | Ct + RT | ΔCt   |
|--------|---------|---------|-------|
| Lung   |         |         |       |
| —      | 35.79   | 23.26   | 12.53 |
| CTAB   | 37.69   | 23.75   | 13.94 |
| TTAB   | 36.61   | 23.41   | 13.20 |
| Kidney |         |         |       |
| —      | 36.02   | 20.10   | 15.92 |
| CTAB   | 37.92   | 20.89   | 17.03 |
| TTAB   | 37.61   | 20.50   | 17.11 |
| Heart  |         |         |       |
| —      | 34.03   | 20.85   | 13.18 |
| CTAB   | 36.67   | 21.09   | 15.58 |
| TTAB   | 36.32   | 21.10   | 15.23 |
| Spleen |         |         |       |
| —      | 33.27   | 21.68   | 11.60 |
| CTAB   | 35.14   | 21.78   | 13.36 |
| TTAB   | 34.55   | 21.59   | 12.97 |
| Brain  |         |         |       |
| —      | 35.69   | 21.44   | 14.25 |
| CTAB   | 36.52   | 21.22   | 15.31 |
| TTAB   | 37.13   | 21.46   | 15.67 |

As can be derived from the higher ΔCt values (see also FIG. 2 *b*), the method according to the present invention considerably reduced the amount of DNA contaminations in the RNA isolated from different tissue samples. Thus, the method according to the present invention is particularly suitable for isolating pure RNA from different tissues.

Example 3

Figure 3:
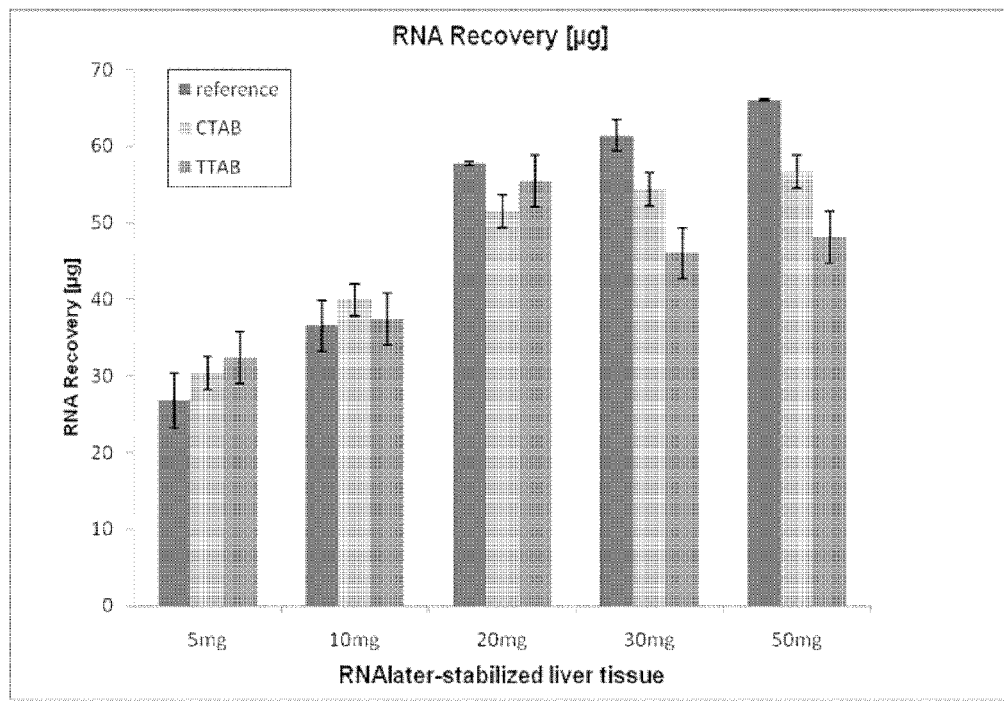
FIG. 3 shows yield of RNA isolated from increasing amounts of RNAlater-stabilized liver tissue measured according to Example 3.
Figure 4:
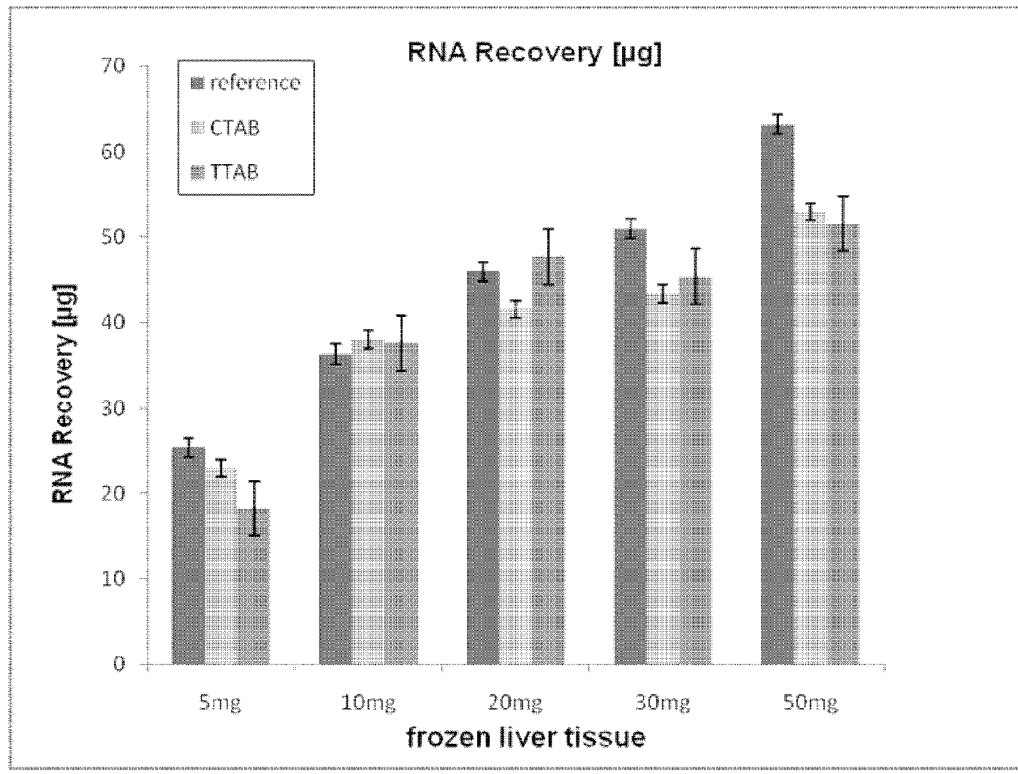
FIG. 4 shows yield of RNA isolated from increasing amounts of frozen liver tissue measured according to Example 3.

RNA was isolated from increasing amounts of tissue using the Qiazol reagent wherein the cationic detergent was directly added to the homogenate according to the following procedure:
1. 5 mg, 10 mg, 20 mg, 30 mg and 50 mg of (a) RNAlater-stabilized liver or (b) frozen liver were homogenized in 1 ml Qiazol reagent using a TissueeRuptor homogenizer.
2. 100 μl of the following detergent stock solutions were added:
   Cetyl-trimethylammonium bromide [1%], CTAB
   Tetra-decyltrimethylammonium bromide [1%], TTAB.
   For the reference, no detergent was added ("reference").
   This was followed by the addition of 200 μl chloroform and vortexing.
3. The samples were centrifuged for 15 min at 12.000×g at 4° C., the resulting aqueous phase was transferred into new Eppendorf tubes.
4. The supernatant was mixed with 1.5 volumes of absolute ethanol and the aqueous phase was transferred onto RNeasy mini columns (Qiagen) and centrifuged for 15 s at 8.200×g, followed by a wash with 700 μl RWT buffer (Qiagen) and subsequent centrifugation, 15 s at 8.200×g.
5. The columns were washed twice with 500 μl RPE buffer (Qiagen) at 8.200×g for 15 s and 2 minutes respectively, followed by a final centrifugation step at maximum speed for 1 minute.
6. Bound RNA was eluted into 30 μl RNase-free water by centrifugation at 8.200×g for 1 min and the RNA concentration is determined spectroscopically using a NanoDrop (ThermoScientific). The results are shown in Tables 7 and 8 and FIGS. 3 and 4.

TABLE 7

RNA isolated from increasing amounts of RNAlater-stabilized liver tissue. The amount of tissue varied from 5 mg to 50 mg. The RNA yield was also plotted as bar graphs (see FIG. 3).

| detergent | Tissue [mg] | A260   | A280   | 260/280 | 260/230 | ng/μl | Yield [μg] | Mean [μg] |
|-----------|-------------|--------|--------|---------|---------|-------|------------|-----------|
| —         | 5 mg        | 24.452 | 11.957 | 2.05    | 1.78    | 978.1 | 29.34      | 26.78     |
| —         |             | 20.184 | 9.772  | 2.07    | 1.67    | 807.4 | 24.22      |           |
| CTAB      | 5 mg        | 27.690 | 13.550 | 2.04    | 1.63    | 1108  | 33.24      | 30.39     |
| CTAB      |             | 22.943 | 11.122 | 2.06    | 1.84    | 917.7 | 27.53      |           |
| TTAB      | 5 mg        | 26.255 | 12.763 | 2.06    | 1.81    | 1050  | 31.50      | 32.37     |
| TTAB      |             | 27.692 | 13.517 | 2.05    | 1.84    | 1108  | 33.24      |           |
| —         | 10 mg       | 32.399 | 15.988 | 2.03    | 1.74    | 1296  | 38.88      | 36.56     |
| —         |             | 28.529 | 14.006 | 2.04    | 1.84    | 1141  | 34.23      |           |
| CTAB      | 10 mg       | 35.878 | 17.622 | 2.04    | 1.65    | 1435  | 43.05      | 39.93     |
| CTAB      |             | 30.673 | 14.941 | 2.05    | 1.75    | 1227  | 36.81      |           |
| TTAB      | 10 mg       | 33.162 | 16.048 | 2.07    | 1.68    | 1326  | 39.78      | 37.37     |
| TTAB      |             | 29.124 | 14.254 | 2.04    | 1.66    | 1165  | 34.95      |           |
| —         | 20 mg       | 47.934 | 23.695 | 2.02    | 1.88    | 1917  | 57.51      | 57.72     |
| —         |             | 48.286 | 23.939 | 2.02    | 1.91    | 1931  | 57.93      |           |
| CTAB      | 20 mg       | 42.961 | 21.064 | 2.04    | 1.94    | 1718  | 51.54      | 51.50     |
| CTAB      |             | 42.875 | 21.048 | 2.04    | 1.93    | 1715  | 51.45      |           |
| TTAB      | 20 mg       | 50.276 | 24.630 | 2.04    | 1.87    | 2011  | 60.33      | 55.46     |
| TTAB      |             | 42.155 | 20.318 | 2.07    | 1.94    | 1686  | 50.58      |           |
| —         | 30 mg       | 52.353 | 25.974 | 2.02    | 1.57    | 2094  | 62.82      | 61.40     |
| —         |             | 49.972 | 24.760 | 2.02    | 1.68    | 1999  | 59.97      |           |
| CTAB      | 30 mg       | 47.091 | 23.258 | 2.02    | 1.66    | 1884  | 56.52      | 54.38     |
| CTAB      |             | 43.525 | 21.625 | 2.01    | 1.72    | 1741  | 52.23      |           |

TABLE 7-continued

RNA isolated from increasing amounts of RNAlater-stabilized liver tissue. The amount of tissue varied from 5 mg to 50 mg. The RNA yield was also plotted as bar graphs (see FIG. 3).

| detergent | Tissue [mg] | A260 | A280 | 260/280 | 260/230 | ng/µl | Yield [µg] | Mean [µg] |
|---|---|---|---|---|---|---|---|---|
| TTAB | 30 mg | 39.126 | 19.177 | 2.04 | 1.72 | 1565 | 46.95 | 46.02 |
| TTAB | | 37.573 | 18.623 | 2.02 | 1.76 | 1503 | 45.09 | |
| — | 50 mg | 54.934 | 27.221 | 2.02 | 1.37 | 2197 | 65.91 | 65.99 |
| — | | 55.061 | 27.002 | 2.04 | 1.62 | 2202 | 66.06 | |
| CTAB | 50 mg | 48.503 | 23.899 | 2.03 | 1.54 | 1940 | 58.20 | 56.69 |
| CTAB | | 45.963 | 22.397 | 2.05 | 1.68 | 1839 | 55.17 | |
| TTAB | 50 mg | 42.100 | 20.818 | 2.02 | 1.61 | 1684 | 50.52 | 48.14 |
| TTAB | | 38.122 | 18.843 | 2.02 | 1.73 | 1525 | 45.75 | |

TABLE 8

RNA isolated from increasing amounts of frozen liver tissue. The amount of tissue varied from 5 mg to 50 mg. The RNA yield was also plotted as bar graphs (see FIG. 4).

| detergent | Tissue [mg] | A260 | A280 | 260/280 | 260/230 | ng/µl | Yield [µg] | Mean |
|---|---|---|---|---|---|---|---|---|
| — | 5 mg | 22.364 | 10.897 | 2.05 | 1.79 | 894.6 | 26.84 | 25.35 |
| — | | 19.890 | 9.507 | 2.09 | 1.66 | 795.6 | 23.87 | |
| CTAB | 5 mg | 20.513 | 10.067 | 2.04 | 1.84 | 820.5 | 24.62 | 22.95 |
| CTAB | | 17.732 | 8.776 | 2.02 | 1.83 | 709.3 | 21.28 | |
| TTAB | 5 mg | 15.694 | 7.761 | 2.02 | 1.85 | 627.8 | 18.83 | 18.22 |
| TTAB | | 14.671 | 7.324 | 2.00 | 1.75 | 586.8 | 17.60 | |
| — | 10 mg | 34.160 | 16.683 | 2.05 | 1.91 | 1366 | 40.98 | 36.30 |
| — | | 26.352 | 12.897 | 2.04 | 1.85 | 1054 | 31.62 | |
| CTAB | 10 mg | 28.975 | 14.074 | 2.06 | 1.86 | 1159 | 34.77 | 38.04 |
| CTAB | | 34.420 | 16.551 | 2.08 | 1.88 | 1377 | 41.31 | |
| TTAB | 10 mg | 33.370 | 16.137 | 2.07 | 1.90 | 1335 | 40.05 | 37.56 |
| TTAB | | 29.217 | 14.178 | 2.06 | 1.90 | 1169 | 35.07 | |
| — | 20 mg | 40.552 | 19.820 | 2.05 | 1.65 | 1622 | 48.66 | 45.93 |
| — | | 36.012 | 17.575 | 2.05 | 1.75 | 1440 | 43.20 | |
| CTAB | 20 mg | 32.167 | 15.513 | 2.07 | 1.83 | 1287 | 38.61 | 41.58 |
| CTAB | | 37.117 | 18.403 | 2.02 | 1.87 | 1485 | 44.55 | |
| TTAB | 20 mg | 42.320 | 20.829 | 2.03 | 1.82 | 1693 | 50.79 | 47.67 |
| TTAB | | 37.131 | 18.027 | 2.06 | 1.74 | 1485 | 44.55 | |
| — | 30 mg | 44.764 | 21.929 | 2.04 | 1.71 | 1791 | 53.73 | 50.93 |
| — | | 40.108 | 19.658 | 2.04 | 1.82 | 1604 | 48.12 | |
| CTAB | 30 mg | 36.568 | 17.965 | 2.04 | 1.66 | 1463 | 43.89 | 43.32 |
| CTAB | | 35.634 | 17.471 | 2.04 | 1.68 | 1425 | 42.75 | |
| TTAB | 30 mg | 32.383 | 15.709 | 2.06 | 1.82 | 1295 | 38.85 | 45.36 |
| TTAB | | 43.215 | 21.409 | 2.02 | 1.85 | 1729 | 51.87 | |
| — | 50 mg | 51.985 | 25.841 | 2.01 | 1.59 | 2079 | 62.37 | 63.18 |
| — | | 53.315 | 26.260 | 2.03 | 1.72 | 2133 | 63.99 | |
| CTAB | 50 mg | 44.704 | 21.817 | 2.05 | 1.79 | 1788 | 53.64 | 52.92 |
| CTAB | | 43.495 | 21.121 | 2.06 | 1.73 | 1740 | 52.20 | |
| TTAB | 50 mg | 44.839 | 21.898 | 2.05 | 1.84 | 1794 | 53.82 | 51.54 |
| TTAB | | 41.056 | 20.090 | 2.04 | 1.66 | 1642 | 49.26 | |

7. RNA integrity was assessed using an Agilent BioAnalyzer 2100, the results are shown Tables 9 and 10.

TABLE 9

RNA integrity of RNA isolated from RNAlater-stabilzed tissue assayed by an Agilent BioAnalyzer 2100:

| | detergent | | | | | |
|---|---|---|---|---|---|---|
| amount tissue | — 5 mg | CTAB 5 mg | TTAB 5 mg | — 10 mg | CTAB 10 mg | TTAB 10 mg |
| RNA Area | 377.1 | 441.4 | 511.4 | 574.5 | 552.1 | 582.6 |
| RNA Conc. | 173 ng/µl | 203 ng/µl | 235 ng/µl | 264 ng/µl | 253 ng/µl | 267 ng/µl |
| ratio [28 s/18 s] | 1.6 | 1.6 | 1.6 | 1.5 | 1.7 | 1.5 |
| RIN | 9.40 | 9.60 | 9.60 | 9.30 | 9.70 | 9.40 |

TABLE 9-continued

RNA integrity of RNA isolated from RNAlater-stabilzed tissue assayed by an Agilent BioAnalyzer 2100:

| | detergent | | | | | |
|---|---|---|---|---|---|---|
| amount tissue | —<br>20 mg | CTAB<br>20 mg | TTAB<br>20 mg | —<br>30 mg | CTAB<br>30 mg | TTAB<br>30 mg |
| RNA Area | 1109.6 | 955.9 | 806.6 | 967 | 991.4 | 749.4 |
| RNA Conc. | 509 ng/µl | 439 ng/µl | 370 ng/µl | 444 ng/µl | 455 ng/µl | 344 ng/µl |
| ratio [28 s/18 s] | 1.5 | 1.5 | 1.5 | 1.6 | 1.6 | 1.4 |
| RIN | 9.10 | 9.40 | 9.40 | 9.10 | 9.10 | 8.90 |

TABLE 10

RNA integrity of RNA isolated from frozen tissue samples assayed by an Agilent BioAnalyzer 2100:

| | detergent | | | | | |
|---|---|---|---|---|---|---|
| amount tissue | —<br>No. 1 | CTAB<br>No. 2 | TTAB<br>No. 3 | —<br>No. 4 | CTAB<br>No. 5 | TTAB<br>No. 6 |
| RNA Area | 313.8 | 329.7 | 273.7 | 656.9 | 517.0 | 557.8 |
| RNA Conc. | 165 ng/µl | 173 ng/µl | 144 ng/µl | 345 ng/µl | 272 ng/µl | 293 ng/µl |
| ratio [28 s/18 s] | 1.7 | 1.8 | 1.7 | 1.8 | 1.8 | 1.8 |
| RIN | 9.80 | 9.70 | 9.80 | 9.60 | 9.60 | 9.70 |
| | detergent | | | | | |
| amount tissue | —<br>No. 7 | CTAB<br>No. 8 | TTAB<br>No. 9 | —<br>No. 10 | CTAB<br>No. 11 | TTAB<br>No. 12 |
| RNA Area | 681 | 629.9 | 715.4 | 776.7 | 641.6 | 638.9 |
| RNA Conc. | 358 ng/µl | 331 ng/µl | 376 ng/µl | 408 ng/µl | 337 ng/µl | 336 ng/µl |
| ratio [28 s/18 s] | 1.9 | 1.9 | 1.9 | 1.9 | 1.9 | 2.0 |
| RIN | 9.60 | 9.50 | 9.70 | 9.70 | 9.70 | 9.50 |

As can be seen, the RIN value is excellent for the RNA isolated by the method according to the present invention.

Figure 5:
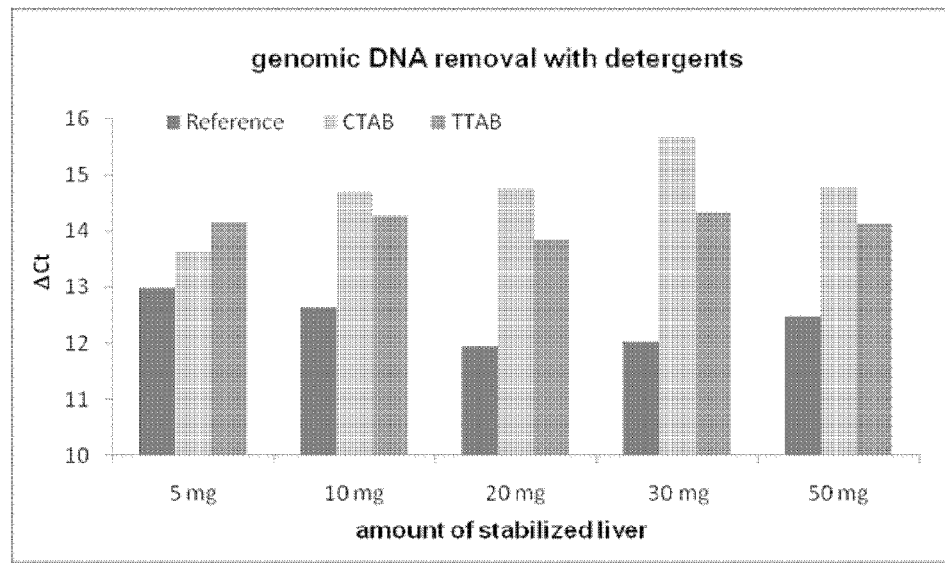
FIG. 5 shows results of qRT-PCR using the "QuantiTect RT-PCR" kit (Qiagen) to assess genomic DNA co-purification and thus contamination during RNA isolation from RNAlater-stabilized (a) and frozen liver tissue (b) using no detergent ("reference"), CTAB, or TTAB measured according to Example 3.
Figure 5:
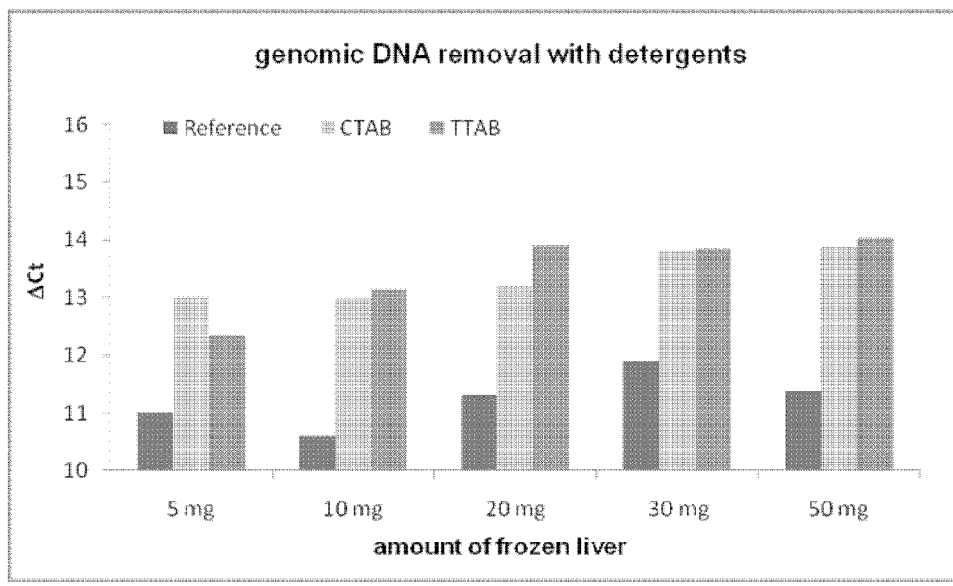

8. RNA samples were diluted 1:70 with RNase-free water. 2 µl of this dilution were then reverse transcribed with 10 pmole gene-specific primer and probe (PGK1 primer mix, PGK1 probe) each using a QuantiTect RT-PCR kit (Qiagen) with and without reverse transcriptase in a reaction volume of 25 µl:
(1) 30 min @50° C.
(2) 15 min @95° C.
(3) 15 s @95° C.
(4) 1 min @60° C., repeat steps (3), (4) for 40 cycles.
The resulting Ct and ΔCt values are listed in Table 11 a) and b) and are plotted as bar graphs in FIGS. 5 a) and b).

TABLE 11 a) and b)

qRT-PCR assays using the "QuantiTect RT-PCR" kit (Qiagen) to assess genomic DNA co-purification and thus contamination during RNA isolation from RNAlater-stabilized ((a)) and frozen liver tissue ((b)) using no detergent ("—"), CTAB or TTAB as indicated from increasing amounts of tissue. The bar graphs shown in FIG. 5 a) and b) illustrate the decrease of genomic DNA according to the ΔCt values shown in Table 11 a) and b).

a)

| | RNAlater-stabilized | | | |
|---|---|---|---|---|
| detergent | amount tissue | Ct − RT | Ct + RT | Δct |
| — | 5 mg | 36.53 | 23.54 | 12.99 |
| CTAB | 5 mg | 36.89 | 23.25 | 13.64 |
| TTAB | 5 mg | 37.36 | 23.22 | 14.14 |
| — | 10 mg | 35.19 | 22.56 | 12.63 |
| CTAB | 10 mg | 37.67 | 22.98 | 14.70 |
| TTAB | 10 mg | 37.11 | 22.84 | 14.28 |
| — | 20 mg | 34.38 | 22.44 | 11.94 |
| CTAB | 20 mg | 36.95 | 22.19 | 14.76 |
| TTAB | 20 mg | 36.45 | 22.61 | 13.84 |
| — | 30 mg | 34.88 | 22.85 | 12.04 |
| CTAB | 30 mg | 38.29 | 22.62 | 15.67 |
| TTAB | 30 mg | 36.80 | 22.47 | 14.33 |
| — | 50 mg | 34.67 | 22.19 | 12.48 |
| CTAB | 50 mg | 37.29 | 22.52 | 14.77 |
| TTAB | 50 mg | 36.70 | 22.58 | 14.13 | b)

| | frozen liver | | | |
|---|---|---|---|---|
| detergent | amount tissue | Ct − RT | Ct + RT | Δct |
| — | 5 mg | 34.80 | 23.78 | 11.02 |
| CTAB | 5 mg | 36.53 | 23.52 | 13.01 |
| TTAB | 5 mg | 36.46 | 24.11 | 12.35 |
| — | 10 mg | 33.85 | 23.24 | 10.61 |
| CTAB | 10 mg | 35.97 | 23.00 | 12.97 |
| TTAB | 10 mg | 36.35 | 23.21 | 13.14 |
| — | 20 mg | 34.07 | 22.77 | 11.31 |
| CTAB | 20 mg | 36.28 | 23.08 | 13.20 |
| TTAB | 20 mg | 36.85 | 22.94 | 13.91 |

TABLE 11 a) and b)-continued qRT-PCR assays using the "QuantiTect RT-PCR" kit (Qiagen) to assess genomic DNA co-purification and thus contamination during RNA isolation from RNAlater-stabilized ((a)) and frozen liver tissue ((b)) using no detergent ("—"), CTAB or TTAB as indicated from increasing amounts of tissue. The bar graphs shown in FIG. 5 a) and b) illustrate the decrease of genomic DNA according to the ΔCt values shown in Table 11 a) and b).

| | | | | |
|---|---|---|---|---|
| — | 30 mg | 34.66 | 22.75 | 11.91 |
| CTAB | 30 mg | 36.59 | 22.78 | 13.81 |
| TTAB | 30 mg | 36.37 | 22.52 | 13.85 |
| — | 50 mg | 33.94 | 22.56 | 11.38 |
| CTAB | 50 mg | 36.10 | 22.21 | 13.89 |
| TTAB | 50 mg | 36.46 | 22.43 | 14.03 |

Example 4

The effect on genomic DNA co-purification during RNA isolation was assessed using varying amounts of a cationic detergent, which was directly added to the homogenate according to the following procedure with four individual RNA preparations per condition:

1. 930 mg of RNAlater-stabilized liver were homogenized in 31 ml Qiazol reagent using a TissueRuptor homogenizer.
2. Homogenates, 1000 µl each (corresponds to 30 mg liver), were aliquoted into 2 ml Eppendorf tubes and either no detergent or increasing amounts of a 1% CTAB stock solution were added to the samples: 50 µl, 100 µl, 150 µl, 200 µl followed by adding of 200 µl chloroform and vortexing.
3. The samples were centrifuged for 15 min at 12.000×g at 4° C., the resulting aqueous phase was transferred into new Eppendorf tubes.
4. The supernatant was mixed with 1.5 volumes of absolute ethanol and the aqueous phase was transferred onto RNeasy mini columns (Qiagen), centrifuged for 15 s at 8.200×g, followed by a wash with 700 µl RVVT buffer (Qiagen) and subsequent centrifugation, 15 s at 8.200×g.
5. The columns were then washed twice with 500 µl RPE buffer (Qiagen) at 8.200×g for 15 s and 2 minutes respectively, followed by a final centrifugation step at maximum speed for 1 minute.
6. Bound RNA was eluted into 30 µl RNase-free water by centrifugation at 8.200×g for 1 min and the RNA concentration was determined using a NanoDrop spectrometer (ThermoScientific). The results are shown in Table 12 and FIG. 6.

TABLE 12

Influence of increasing amounts of CTAB during RNA extraction on RNA recovery.

| µl CTAB | A260 | A280 | 260/280 | 260/230 | ng/µl | Yield [µg] | Mean |
|---|---|---|---|---|---|---|---|
| reference | 61.772 | 30.792 | 2.01 | 1.84 | 2471 | 74.13 | 71.97 |
| reference | 61.338 | 30.397 | 2.02 | 1.76 | 2454 | 73.62 | |
| reference | 54.492 | 26.881 | 2.03 | 1.75 | 2180 | 65.40 | |
| reference | 62.267 | 30.651 | 2.03 | 1.76 | 2491 | 74.73 | |
| 50 µl | 56.441 | 27.980 | 2.02 | 1.77 | 2258 | 67.74 | 60.97 |
| 50 µl | 50.333 | 24.700 | 2.04 | 1.84 | 2013 | 60.39 | |
| 50 µl | 37.408 | 18.097 | 2.07 | 1.91 | 1496 | 44.88 | |
| 50 µl | 59.050 | 29.230 | 2.02 | 1.82 | 2362 | 70.85 | |
| 100 µl | 54.058 | 26.644 | 2.03 | 1.74 | 2152 | 64.85 | 60.11 |
| 100 µl | 52.015 | 25.405 | 2.05 | 1.78 | 2081 | 62.43 | |
| 100 µl | 45.635 | 22.325 | 2.04 | 1.80 | 1825 | 54.75 | |
| 100 µl | 48.680 | 23.947 | 2.03 | 1.82 | 1947 | 58.41 | |
| 150 µl | 52.744 | 26.175 | 2.02 | 1.64 | 2110 | 63.30 | 56.39 |
| 150 µl | 46.100 | 22.432 | 2.05 | 1.83 | 1844 | 55.32 | |
| 150 µl | 44.619 | 21.694 | 2.05 | 1.90 | 1785 | 53.55 | |
| 150 µl | 44.492 | 21.652 | 2.05 | 1.81 | 1780 | 53.40 | |
| 200 µl | 41.886 | 20.785 | 2.02 | 1.76 | 1675 | 50.25 | 50.55 |
| 200 µl | 41.403 | 20.379 | 2.03 | 1.80 | 1656 | 49.68 | |
| 200 µl | 42.729 | 20.774 | 2.05 | 1.79 | 1709 | 51.27 | |
| 200 µl | 42.509 | 20.974 | 2.03 | 1.84 | 1700 | 51.00 | |

Four independent RNA isolations were done for each condition. "Reference" indicates that no CTAB was added during the RNA isolation.

Figure 6:
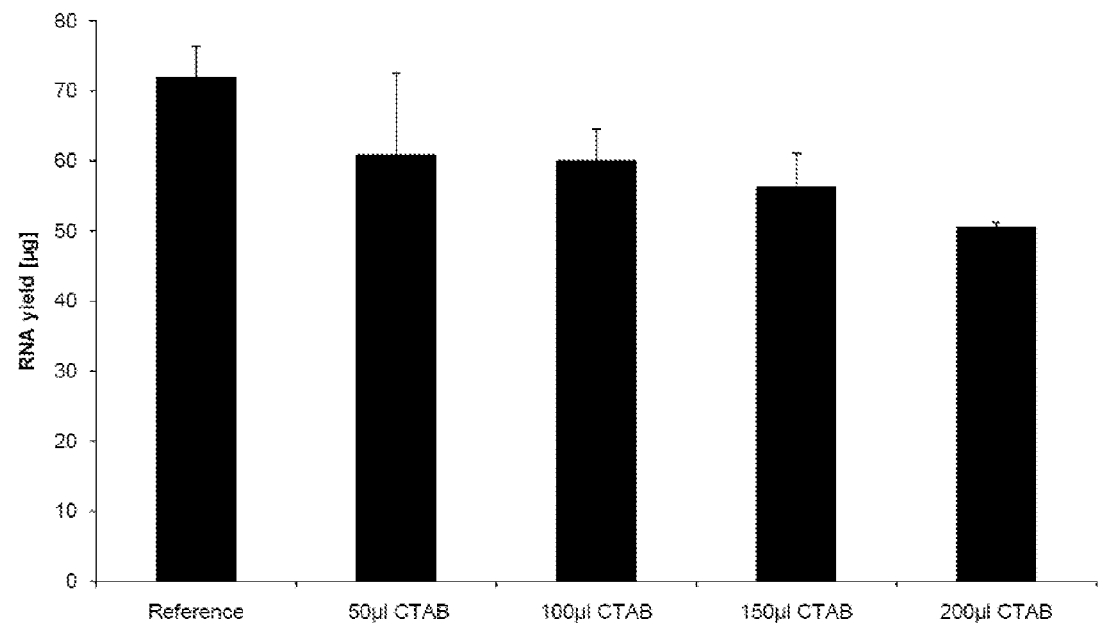
FIG. 6 shows influence of increasing amounts of CTAB during RNA extraction on RNA recovery analyzed according to Example 4.

The results are also summarised in FIG. 6. The presumable decrease in RNA yield between the reference method and the method according to the present invention is largely attributable to a decrease of genomic DNA in the isolated RNA, and not to a decrease of RNA, what is inter alia supported by the qRT-PCR assays (see FIG. 7) and the other examples presented herein.

7. RNA integrity was assessed using an Agilent BioAnalyzer 2100. The results are shown in Table 13.

TABLE 13

Effects of increasing amounts of CTAB on RNA integrity. RNA eluates were diluted 1:10 with RNAse-free water and analyzed using an Agilent Bioanalyzer 2100.

| µl CTAB | reference | reference | 50 µl | 50 µl | 100 µl | 100 µl | 150 µl | 150 µl |
|---|---|---|---|---|---|---|---|---|
| RNA Area | 338.6 | 433.3 | 378.5 | 356.2 | 305.3 | 309.5 | 337.8 | 249.7 |
| RNA Conc. | 138 ng/µl | 177 ng/µl | 154 ng/µl | 145 ng/µl | 124 ng/µl | 126 ng/µl | 138 ng/µl | 102 ng/µl |
| ratio [28 s/18 s] | 1.6 | 1.6 | 1.6 | 1.6 | 1.6 | 1.6 | 1.6 | 1.6 |
| RIN | 9.50 | 9.50 | 9.50 | 9.50 | 9.50 | 9.50 | 9.50 | 9.50 |

8. RNA samples were diluted 1:90 with RNase-free water and reverse transcribed with 10 pmole gene-specific primer and probe each (PGK1 primer mix, PGK1 probe) using a QuantiTect RT-PCR kit (Qiagen) with and without reverse transcriptase in a reaction volume of 25 µl:
   (1) 30 min @50° C.
   (2) 15 min @95° C.
   (3) 15 s @95° C.
   (4) 1 min @60° C., repeat steps (3), (4) for 40 cycles.
The resulting Ct and ΔCt values are shown in Table 14 and corresponding FIG. 7.

TABLE 14

Removal of genomic DNA quantified by increasing amounts of CTAB during RNA isolation by qRT-PCR assays using the "QuantiTect RT-PCR" kit (Qiagen) by increasing the amounts of CTAB assessed by qRT-PCR. The qRT-PCR assays were done according to example 4.

|  | Ct − RT | Ct + RT | Δct |
|---|---|---|---|
| Reference | 36.79 | 23.46 | 13.33 |
| 50 μl CTAB | 38.21 | 23.57 | 14.64 |
| 100 μl CTAB | 38.61 | 23.73 | 14.88 |
| 150 μl CTAB | 39.35 | 23.60 | 15.75 |
| 200 μl CTAB | 38.77 | 23.55 | 15.22 |

Figure 7:
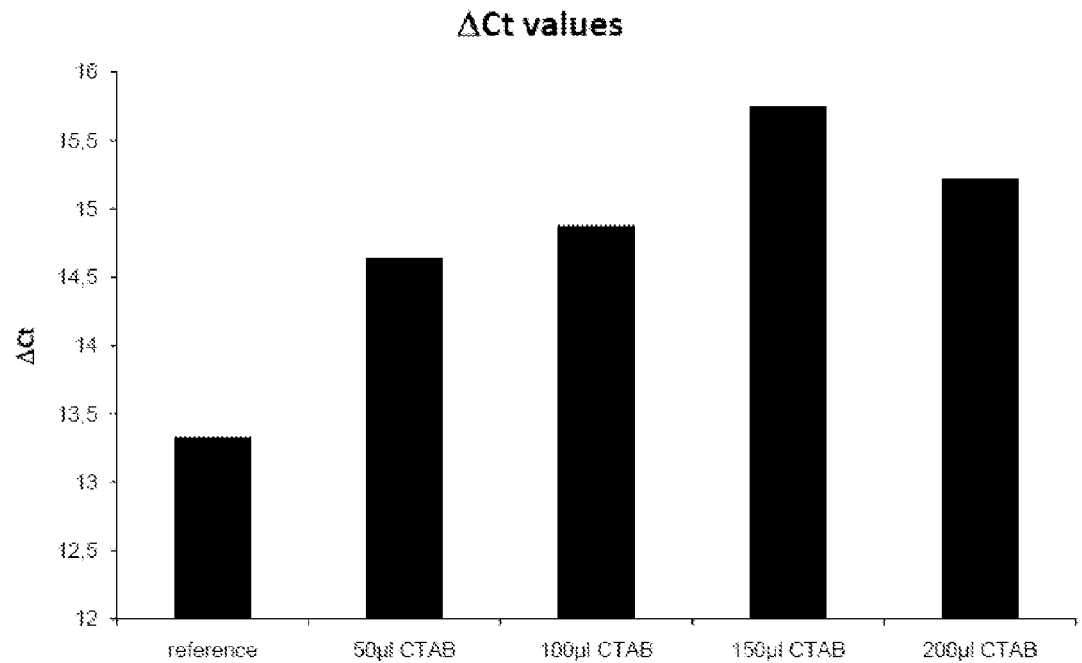
FIG. 7 shows removal of genomic DNA by increasing amounts of CTAB during RNA isolation by qRT-PCR assays using the "QuantiTect RT-PCR" kit (Qiagen) by increasing the amounts of CTAB assessed by qRT-PCR according to Example 4.

The results are also illustrated by FIG. 7. As can be seen, increasing the amount of CTAB resulted in an increased reduction of DNA contaminations in the isolated RNA.

Example 5

To compare the effect on genomic DNA co-purification during RNA isolation from tissue using two different cationic detergent solutions (CTAB and buffer "BB" (Qiagen, contains 1% CTAB and a salt)) the following experiment was carried out:

1. 425 mg of RNAlater-stabilized spleen and 425 mg of frozen spleen were homogenized in 31 ml Qiazol reagent each using a TissueRuptor homogenizer.
2. Homogenates, 1000 μl each, were aliquoted into 2 ml Eppendorf tubes and 100 μl of the following stock solutions were directly added to the homogenate: Cetyl-trimethylammonium bromide [1%], CTAB Qiagen buffer BB (1% CTAB in NaCl)
   For the reference, no detergent was added ("reference").
   This was followed by the addition of 200 μl chloroform and vortexing.
3. The samples were centrifuged for 15 min at 12.000×g at 4° C. and the resulting aqueous phase was transferred into a new Eppendorf tube.
4. The supernatant was mixed with 1.5 volumes of absolute ethanol and the aqueous phase was transferred onto RNeasy mini columns (Qiagen) and centrifuged for 15 s at 8.200×g, followed by a wash with 700 μl RVVT buffer (Qiagen) and subsequent centrifugation for 15 s at 8.200×g.
5. The columns were then washed twice with 500 μl RPE buffer (Qiagen) at 8.200×g for 15 s and 2 minutes respectively, followed by a final centrifugation step at maximum speed for 1 minute.
6. Bound RNA was eluted into 30 μl RNase-free water by centrifugation at 8.200×g for 1 min and the RNA concentration was determined spectroscopically using a NanoDrop (ThermoScientific). The results are shown in Table 15.

TABLE 15

Quantification of RNA isolated from RNAlater-stabilized ("RNAlater") or frozen ("frozen") spleen using two different cationic detergent-containing compositions, which were directly added to the homogenate.

| tissue | buffer | A260 | A280 | A260/280 | A260/230 | ng/μl | yield [μg] | Mean |
|---|---|---|---|---|---|---|---|---|
| RNAlater | Reference | 71.422 | 36.032 | 1.98 | 1.91 | 2857 | 85.71 | 81.68 |
|  |  | 69.842 | 35.012 | 1.99 | 1.89 | 2794 | 83.82 |  |
|  |  | 61.597 | 30.460 | 2.02 | 1.91 | 2464 | 73.92 |  |
|  |  | 70.124 | 35.122 | 2.00 | 1.97 | 2805 | 84.15 |  |
|  |  | 67.317 | 33.899 | 1.99 | 1.97 | 2693 | 80.79 |  |
| RNAlater | 100 μl CTAB | 72.124 | 36.581 | 1.97 | 1.99 | 2885 | 86.55 | 87.45 |
|  |  | 149.061 | 73.708 | 2.02 | 2.02 | 5962 | 178.86 |  |
|  |  | 73.858 | 36.688 | 2.01 | 1.99 | 2954 | 88.62 |  |
|  |  | 72.922 | 37.341 | 1.95 | 1.98 | 2917 | 87.51 |  |
|  |  | 72.588 | 36.490 | 1.99 | 2.01 | 2904 | 87.12 |  |
| RNAlater | 100 μl BB-buffer | 76.363 | 38.307 | 1.99 | 1.99 | 3055 | 91.65 | 84.30 |
|  |  | 74.162 | 37.259 | 1.99 | 1.98 | 2966 | 88.98 |  |
|  |  | 73.515 | 37.149 | 1.98 | 1.99 | 2941 | 88.23 |  |
|  |  | 60.654 | 30.132 | 2.01 | 1.98 | 2426 | 72.78 |  |
|  |  | 66.558 | 32.823 | 2.03 | 2.06 | 2662 | 79.86 |  |
| frozen | reference | 60.330 | 30.174 | 2.00 | 1.83 | 2413 | 72.39 | 65.43 |
|  |  | 51.787 | 26.151 | 1.98 | 1.86 | 2071 | 62.13 |  |
|  |  | 53.694 | 27.049 | 1.99 | 1.85 | 2148 | 64.44 |  |
|  |  | 49.318 | 24.708 | 2.00 | 1.67 | 1973 | 59.19 |  |
|  |  | 57.510 | 29.020 | 1.98 | 1.85 | 2300 | 69.00 |  |
| frozen | 100 μl CTAB | 58.830 | 29.681 | 1.98 | 1.87 | 2353 | 70.59 | 69.54 |
|  |  | 51.649 | 25.876 | 2.00 | 1.92 | 2066 | 61.98 |  |
|  |  | 58.727 | 29.401 | 2.00 | 1.94 | 2349 | 70.47 |  |
|  |  | 60.331 | 30.073 | 2.01 | 1.92 | 2413 | 72.39 |  |
|  |  | 60.223 | 30.488 | 1.98 | 1.71 | 2409 | 72.27 |  |
| frozen | 100 μl BB-buffer | 50.196 | 25.252 | 1.99 | 1.91 | 2008 | 60.24 | 64.54 |
|  |  | 53.888 | 26.953 | 2.00 | 1.92 | 2156 | 64.68 |  |
|  |  | 49.138 | 24.273 | 2.02 | 1.89 | 1966 | 58.98 |  |
|  |  | 59.651 | 30.126 | 1.98 | 1.92 | 2386 | 71.58 |  |
|  |  | 55.991 | 28.220 | 1.98 | 1.92 | 2240 | 67.20 |  |

"Reference" indicates that no detergent or buffer was added. Four independent RNA preparations were carried out for each tested condition.

7. RNA integrity was assessed using an Agilent BioAnalyzer 2100, see Table 16.

TABLE 16

Comparison of RNA integrity of RNA isolated from RNAlater-stabilized and frozen spleen according to example 5. RNA eluates were diluted 1:10 into RNAse-free water prior to running them on an Agilent Bioanalyzer 2100.

|  | reference | reference | CTAB | CTAB | BB | BB |
|---|---|---|---|---|---|---|
| RNAlater |  |  |  |  |  |  |
| RNA Area | 536.4 | 525.2 | 717.9 | 666.0 | 891.9 | 605.3 |
| RNA Conc. | 267 ng/μl | 262 ng/μl | 357 ng/μl | 332 ng/μl | 444 ng/μl | 301 ng/μl |
| ratio [28 s/18 s] | 1.3 | 1.5 | 1.4 | 1.3 | 1.6 | 1.5 |
| RIN | 7.0 | 7.90 | 8.50 | 8.40 | 9.30 | 8.80 |
| frozen |  |  |  |  |  |  |
| RNA Area | 446.8 | 351.6 | 434.9 | 422 | 358 | 409.3 |
| RNA Conc. | 222 ng/μl | 175 ng/μl | 217 ng/μl | 210 ng/μl | 178 ng/μl | 204 ng/μl |
| ratio [28 s/18 s] | 1.0 | 1.3 | 1.5 | 1.6 | 1.6 | 1.7 |
| RIN | 6.0 | 7.0 | 7.60 | 8.0 | 8.10 | 8.0 |

As can be seen, the RNA integrety is improved when isolating RNA from said tissue using the method according to the present invention.

8. RNA samples were diluted 1:100 with RNase-free water and reverse transcribed with gene-specific primers (PGK1 primer mix and PGK1 probe) at a concentration of 10 μM each using a QuantiTect RT-PCR kit (Qiagen) with and without reverse transcriptase in a reaction volume of 25 μl:
   (1) 30 min@50° C.
   (2) 15 min@95° C.
   (3) 15 s@95° C.
   (4) 1 min@60° C., repeat steps (3), (4) for 40 cycles.
The resulting Ct and ΔCt values are shown in Table 17 and corresponding FIG. 8.

TABLE 17

Comparison of genomic DNA co-purification from RNAlater-stabilized ("RNAlater") and frozen ("frozen") spleen using CTAB or buffer BB as additive. "Ref." indicates the use of Qiazol reagent with no CTAB or buffer BB added. "−RT" and "+RT" indicate qRT-PCR assays without and with reverse transcriptase.

|  | Ct − RT | Ct + RT | Δct |
|---|---|---|---|
| RNAlater ref. | 34.04 | 23.62 | 10.42 |
| RNAlater CTAB | 35.39 | 23.57 | 11.83 |
| RNAlater BB | 35.59 | 23.25 | 12.34 |
| frozen ref. | 34.02 | 24.19 | 9.83 |
| frozen CTAB | 35.42 | 24.01 | 11.41 |
| frozen BB | 35.81 | 24.15 | 11.66 |

Figure 8:
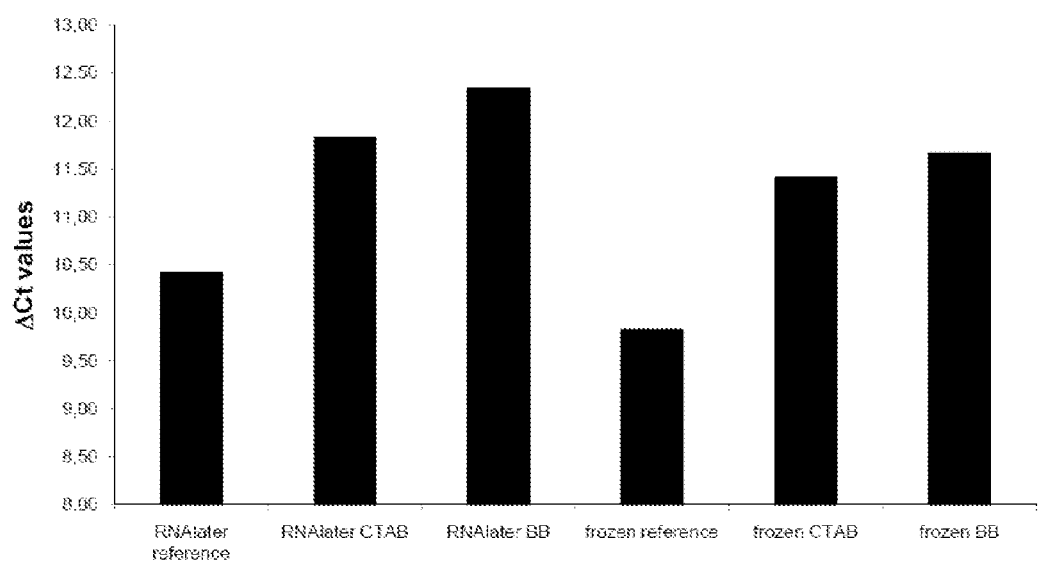
FIG. 8 shows comparison of genomic DNA co-purification from RNAlater-stabilized ("RNAlater") and frozen ("frozen") spleen using CTAB or buffer BB as additive performed according to Example 5.

As can be derived from Table 17 and FIG. 8, the method according to the present invention improves the purity of the RNA isolated from the respective tissue by decreasing the amount of DNA contaminations. This can be derived from the increased ΔCt values.

Example 6

Herein, RNA isolation was performed according to the reference protocol using QIAzol (comprising phenol and a chaotropic agent, but no CTAB), the present invention (wherein CTAB is added to the homogenate), and according to the prior art, wherein only phenol and CTAB is used, but no chaotropic agent (see e.g. EP 1 219 707). This example shows that the combination of the acidic denaturing composition comprising a chaotropic agent and phenol with a cationic detergent is decisive for efficiently isolating pure RNA while reducing the amounts of DNA contamination from samples and in particular difficult samples such as tissue samples. The RNA was isolated from the aqueous RNA containing phase using two different methods—by precipitation as well as by purification using RNAeasy mini columns (Qiagen) which comprise a silica membrane.

6.1. The RNA containing aqueous phase for isolating RNA using QIAzol was obtained as follows:
   1. For this experiment, 2×100 mg of RNAlater-stabilized spleen and lung tissue were homogenized in 9 ml of Qiazol reagent using a TissueRuptor.
   2. Homogenates were distributed in either 900 μl aliquots onto 2 ml Eppendorf tubes or in 1000 μl aliquots.
   3. 100 μl of QIAGEN buffer BB (comprises 1% CTAB and a salt) were added to each 900 μl sample. For the reference method using QIAzol alone, no detergent was added. 180 μl chloroform were added to all samples, vortexed, followed by a 2-3 minute incubation at room temperature. The samples were then centrifuged at 12.000×g at 4° C. for 15 minutes and the resulting aqueous phase was transferred into a new Eppendorf tube.

6.2. The RNA containing aqueous phase for isolating RNA using the method according to EP 1 219 707 was obtained as follows:
   1. 2×100 mg of RNAlater-stabilized lung and spleen tissue were homogenized in 9 ml each of a solution containing 8 ml phenol pH 4.3, 2 ml 10% CTAB, 500 μl 2M sodium acetate pH 4.0, 9.48 ml RNase-free water.
   2. Homogenates (1000 μl) were then transferred into 2 ml Eppendorf tubes. The amount of tissue in the homogenate was the same as with the other methods. 200 μl chloroform was added followed by vortexing and incubation for 2-3 minutes at room temperature. The samples were then centrifuged for 15 minutes at 12.000×g at 4° C.
   3. The aqueous phase was transferred into new Eppendorf tubes and stored over night at −20° C. until further processing.

6.3. RNA isolation from the RNA containing aqueous phase by precipitation

The aqueous phases obtained according to 6.1 and 6.2 were identically further processed as follows:
   1. The RNA was precipitated by adding 500 μl isopropanol, mixing and a 10 minute incubation at room temperature followed by a 15 minute centrifugation step at 12.000×g at 4° C.

2. The supernatant was discarded and the RNA pellet was washed once by adding 1 ml of 75% ethanol, vortexing and subsequent centrifugation for 5 minutes at 7500×g at 4° C.
3. The supernatant was discarded, the pellet air dried and resuspended in 30 μl of RNAse-free water at 60° C. for 10 minutes.
4. The resulting RNA was quantified using a Nanodrop (ThermoScientific), see Table 19.

TABLE 18

The results of RNA precipitated according to example 6.3 are shown. "Phenol with CTAB" refers to the method according to EP 1 219 707 using phenol and CTAB, "QIAzol no CTAB" refers to the QIAzol reference method, wherein no CTAB is added and "QIAzol with CTAB" refers to the method according to the present invention.

| Tissue | Extraction | Purification | A260 | A280 | 260/280 | 260/230 | ng/μl | RNA yield [μg] | Mean |
|---|---|---|---|---|---|---|---|---|---|
| spleen | phenol with CTAB | precipitation | 0.331 | 0.238 | 1.39 | 1.5 | 13.24 | 0.40 | 0.92 |
| | | | 1.207 | 0.773 | 1.56 | 1.99 | 48.3 | 1.45 | |
| | | | 0.78 | 0.488 | 1.6 | 2.01 | 31.18 | 0.94 | |
| | | | 0.755 | 0.445 | 1.7 | 1.77 | 30.2 | 0.91 | |
| spleen | QIAzol no CTAB | precipitation | 42.505 | 22.024 | 1.93 | 1.56 | 1700 | 51.00 | 58.12 |
| | | | 48.968 | 24.951 | 1.96 | 1.81 | 1959 | 58.77 | |
| | | | 52.727 | 26.941 | 1.96 | 1.92 | 2109 | 63.27 | |
| | | | 49.524 | 25.066 | 1.98 | 1.9 | 1981 | 59.43 | |
| spleen | QIAzol with CTAB | precipitation | 46.864 | 23.918 | 1.96 | 1.74 | 1875 | 56.25 | 56.15 |
| | | | 45.774 | 23.047 | 1.99 | 1.95 | 1831 | 54.93 | |
| | | | 49.143 | 24.577 | 2 | 1.78 | 1966 | 58.98 | |
| | | | 45.367 | 23.141 | 1.96 | 1.65 | 1815 | 54.45 | |
| lung | phenol with CTAB | precipitation | 0.203 | 0.128 | 1.58 | 2.07 | 8.103 | 0.24 | 0.31 |
| | | | 0.184 | 0.126 | 1.46 | 2.17 | 7.363 | 0.22 | |
| | | | 0.398 | 0.285 | 1.4 | 2 | 15.91 | 0.48 | |
| | | | 0.238 | 0.202 | 1.18 | 1.74 | 9.537 | 0.29 | |
| lung | QIAzol no CTAB | precipitation | 20.544 | 10.63 | 1.93 | 1.56 | 821.8 | 24.65 | 23.35 |
| | | | 20.373 | 10.682 | 1.91 | 1.57 | 814.9 | 24.45 | |
| | | | 17.786 | 9.504 | 1.87 | 1.63 | 711.4 | 21.34 | |
| | | | 19.137 | 9.485 | 2.02 | 1.63 | 765.5 | 22.97 | |
| lung | QIAzol with CTAB | precipitation | 17.027 | 9.044 | 1.88 | 1.37 | 681.1 | 20.43 | 20.41 |
| | | | 17.696 | 9.282 | 1.91 | 1.54 | 707.9 | 21.24 | |
| | | | 17.516 | 8.973 | 1.95 | 1.6 | 700.6 | 21.02 | |
| | | | 15.795 | 8.339 | 1.89 | 1.55 | 631.8 | 18.95 | |

The results show, that the method according to EP 1 219 707, wherein phenol and CTAB but no chaotropic agent is used is not suitable to isolate RNA from tissue samples.

6.4. RNA isolation from the RNA containing aqueous phase by using RNeasy mini columns (Qiagen):

The aqueous phase was obtained as described above in 6.1 and 6.2. The aqueous phase was then processed as follows:

1. The aqueous phase was mixed with 1.5 volumes of absolute ethanol and transferred onto RNeasy mini columns (Qiagen) and centrifuged for 15 s at 8.200 g. This was followed by a wash with 700 μlRVVT buffer (Qiagen) and subsequent centrifugation for 15 s at 8.200 g.
2. The columns were then washed twice with 500 μl RPE buffer (Qiagen) at 8.200 g for 15 s and 2 minutes respectively, followed by a final centrifugation step at maximum speed for 1 minute.
3. Bound RNA was eluted into 30 μl RNase-free water by centrifugation at 8.200 g for 1 min. The RNA concentration was determined spectroscopically using a NanoDrop (ThermoScientific), see Table 19.

TABLE 19

The results of the RNA isolated according to example 6.4 are shown, the same references are used as in Table 18.

| Tissue | Extraction | Purification | A260 | A280 | 260/280 | 260/230 | ng/μl | RNA yield [μg] | Mean |
|---|---|---|---|---|---|---|---|---|---|
| Spleen | Phenol with CTAB | RNeasy | 0.301 | 0.242 | 1.24 | 0.56 | 12.02 | 0.36 | 0.35 |
| | | | 0.33 | 0.27 | 1.22 | 0.44 | 13.2 | 0.40 | |
| | | | 0.257 | 0.164 | 1.57 | 0.53 | 10.28 | 0.31 | |
| | | | 0.293 | 0.212 | 1.38 | 0.41 | 11.73 | 0.35 | |
| Spleen | QIAzol no CTAB | RNeasy | 31.044 | 16.024 | 1.94 | 1.83 | 1242 | 37.26 | 43.49 |
| | | | 35.821 | 18.197 | 1.97 | 2.02 | 1433 | 42.99 | |
| | | | 39.671 | 19.348 | 2.05 | 2.01 | 1587 | 47.61 | |
| | | | 38.404 | 18.57 | 2.07 | 1.82 | 1536 | 46.08 | |
| Spleen | QIAzol with CTAB | RNeasy | 36.822 | 17.809 | 2.07 | 2.02 | 1473 | 44.19 | 42.52 |
| | | | 39.335 | 19.241 | 2.04 | 1.94 | 1573 | 47.19 | |

TABLE 19-continued

The results of the RNA isolated according to example 6.4 are shown, the same references are used as in Table 18.

| Tissue | Extraction | Purification | A260 | A280 | 260/280 | 260/230 | ng/µl | RNA yield [µg] | Mean |
|---|---|---|---|---|---|---|---|---|---|
|  |  |  | 34.019 | 16.201 | 2.1 | 2.06 | 1361 | 40.83 |  |
|  |  |  | 31.56 | 15.535 | 2.03 | 2.02 | 1262 | 37.86 |  |
| Lung | Pheno with CTABl | RNeasy | 0.094 | 0.043 | 2.19 | 0.35 | 3.762 | 0.11 | 0.16 |
|  |  |  | 0.133 | 0.117 | 1.14 | 0.63 | 5.302 | 0.16 |  |
|  |  |  | 0.189 | 0.186 | 1.02 | 0.63 | 7.567 | 0.23 |  |
|  |  |  | 0.113 | 0.117 | 0.97 | 0.48 | 4.54 | 0.14 |  |
| lung | QIAzol no CTAB | RNeasy | 15.433 | 6.975 | 2.21 | 2.17 | 617.3 | 18.52 | 18.51 |
|  |  |  | 15.944 | 7.566 | 2.11 | 2.23 | 637.8 | 19.13 |  |
|  |  |  | 15.674 | 7.502 | 2.09 | 2.21 | 626.9 | 18.81 |  |
|  |  |  | 14.637 | 6.918 | 2.12 | 2.13 | 585.5 | 17.57 |  |
| lung | QIAzol with CTAB | RNeasy | 15.843 | 7.519 | 2.11 | 2.15 | 633.7 | 19.01 | 18.17 |
|  |  |  | 15.901 | 7.672 | 2.07 | 2.17 | 636 | 19.08 |  |
|  |  |  | 15.4 | 7.636 | 2.02 | 2.07 | 616 | 18.48 |  |
|  |  |  | 13.424 | 6.571 | 2.04 | 2.02 | 537 | 16.11 |  |

6.5. Determination of the genomic DNA content in the isolated RNA qRT-PCRs for assessing the content of genomic DNA contaminations in the RNA isolated according to 6.3 or 6.4 was carried out according to the following steps:
1. RNA samples derived from spleen were diluted to approximately 30 ng/µl, those derived from lung were diluted to ~10 ng/µl.
   RNA samples that were prepared using the phenol formulation according to EP 1 219 707 were not diluted for subsequent qRT-PCR.
2. qRT-PCRs were run in RotoGene Q real-time PCR machines (Qiagen) using the "QuantiFast Probe RT PCR master mix", with 10 pmole of primer and probe (PGK1 primer mix, PGK1 probe) each in a reaction volume of 20 µl with 2 µl of the RNA sample as template. Several independent qRT-PCR reactions were run for each sample. The cycling conditions were:
   (1) 10 minutes@50° C.
   (2) 5 minutes@95° C.
   (3) 10 s@95° C.
   (4) 30 s@60° C., repeat steps (3), (4) 40×

The average Ct and ΔCt values are shown in Table 20.

TABLE 20

Comparison of genomic DNA co-purification in the RNA prepared according to example 6.3 and 6.4, the same references are used as in Tables 18 and 19.

|  | Ct − RT | Ct + RT | Δct |
|---|---|---|---|
| spleen |  |  |  |
| Phenol with CTAB/precipitation | 36.86 | 34.32 | 2.54 |
| Phenol with CTAB/RNeasy | 38.68 | 38.35 | 0.32 |
| QIAzol no CTAB/precipitation | 29.01 | 20.07 | 8.94 |
| QIAzol with CTAB/precipitation | 30.19 | 20.11 | 10.08 |
| QIAzol no CTAB/RNeasy | 28.57 | 21.11 | 7.47 |
| QIAzol with CTAB/RNeasy | 30.18 | 20.91 | 9.27 |
| Lung |  |  |  |
| Phenol with CTAB/precipitation | 40.00 | 40 | 0.00 |
| Phenol with CTAB/RNeasy | 37.43 | 36.25 | 1.18 |
| QIAzol no CTAB/precipitation | 29.99 | 26.51 | 3.48 |
| QIAzol with CTAB/precipitation | 31.31 | 26.60 | 4.71 |
| QIAzol no CTAB/RNeasy | 32.14 | 26.98 | 5.16 |
| QIAzol with CTAB/RNeasy | 34.12 | 27.16 | 6.96 |

As can be seen, the best results are achieved with the method according to the present invention which leads to a considerable reduction in the amount of DNA in the isolated RNA while increasing the amount of isolated (pure) RNA.

The invention claimed is:

1. A method of isolating at least RNA from a sample comprising RNA and DNA, comprising:
   a) lysing or homogenizing a sample comprising RNA and DNA by adding to the sample an acidic denaturing composition comprising a chaotropic agent and phenol;
   b) adding at least one cationic detergent;
   c) adding a water-insoluble organic solvent;
   d) separating the phases of the mixture resulting from steps a) to c) to form a multi-phase mixture comprising an aqueous phase, optionally an interphase, and an organic phase, wherein the RNA is concentrated in said aqueous phase and DNA is concentrated in said organic phase and/or in said interphase; and
   e) isolating said RNA from said aqueous phase of step d); wherein step (c) is performed after step (a), and step (b) is performed before step (d).

2. The method of claim 1, wherein step a) comprises homogenising the sample in the acidic denaturing composition.

3. The method of claim 1, wherein the at least one cationic detergent is added before, at the same time, or after the acidic denaturing composition is added to the sample.

4. The method of claim 1, wherein the at least one cationic detergent is added before or at the same time the water-insoluble organic solvent is added to the sample.

5. The method of claim 1, wherein the at least one cationic detergent is added after the acidic denaturing composition is added to the sample but before the water-insoluble organic solvent is added to the sample.

6. The method of claim 1, wherein said at least one cationic detergent has one or more of the following characteristics:
   (a) it comprises a permanently charged quaternary ammonium cation;
   (b) it comprises ammonium bromide, and/or
   (c) it is selected from the group consisting of CTAB, TTAB, and DTRB.

7. The method of claim 1, wherein said at least one cationic detergent is added in form of a solution.

8. The method of claim 7, wherein said solution has one or more of the following characteristics:
   (a) it comprises the at least one cationic detergent in a concentration selected from the group consisting of 0.1% to 10%, 0.1% to 5%, 0.1% to 3%, and 0.1% to 1%, and/or
   (b) it further comprises a salt.

9. The method of claim 8, wherein the salt of characteristic (b) is selected from the group consisting of sodium chloride, potassium chloride, ammonium chloride, sodium acetate, sodium nitrate, lithium chloride, ammonium sulphate, sodium sulphate, lithium sulphate, potassium sulphate, and mixtures thereof.

10. The method of claim 1, wherein in step b) the multi-phase mixture is formed by centrifuging the mixture at a lower temperature selected from the group consisting of a temperature ≤15° C., a temperature ≤10° C., a temperature ≤7° C., a temperature ≤5° C. and a temperature ≤4° C.

11. The method of claim 1, wherein the RNA is isolated from the aqueous phase by adding at least one alcohol to said aqueous phase.

12. The method of claim 1, wherein the aqueous phase is mixed with an alcohol, and the resulting mixture is contacted with a nucleic acid binding solid phase to bind the RNA.

13. The method of claim 11, wherein the at least one alcohol is selected from the group consisting of methanol, ethanol, propanol, isopropanol and butanol, and/or is added in a concentration selected from the group consisting of at least 20%, at least 30% v/v, at least 40% v/v, at least 50% v/v, and at least 60% v/v.

14. The method of claim 12, wherein the alcohol is selected from the group consisting of methanol, ethanol, propanol, isopropanol and butanol, and/or is added in a concentration selected from the group consisting of at least 20%, at least 30% v/v, at least 40% v/v, at least 50% v/v, and at least 60% v/v.

15. The method of claim 1, wherein the acidic denaturing composition comprising a chaotropic agent and phenol has one or more of the following characteristics:
   (a) the chaotropic agent is a chaotropic salt;
   (b) the chaotropic agent is selected from the group consisting of guanidinium hydrochloride, guanidinium thiocyanate, guanidinium isothiocyanate, sodium thiocyanate, sodium iodide, sodium perchlorate, sodium trichloroacetate, sodium trifluroacetate, and urea;
   (c) the chaotropic agent is comprised in a concentration selected from the group consisting of 0.1 to 6M, 0.5 to 4M, and 0.5 to 3M;
   (d) the phenol is comprised in a concentration selected from the group consisting of 10% v/v to 70% v/v, 20% v/v to 60% v/v, and 30% v/v to 50% v/v;
   (e) it comprises a buffer in an amount sufficient to maintain said composition at an acidic pH;
   (f) it comprises a solubilizer for maintaining the phenol in solution;
   (g) it comprises a thiocyanate component; and/or
   (h) it has a pH value below 6.

16. The method of claim 15, wherein the pH value of characteristic (h) is ≤5.

17. The method of claim 1, wherein the water-insoluble organic solvent is chloroform.

18. A method for reducing the amount of DNA in an RNA-containing aqueous phase and/or increasing the amount of DNA in an interphase and/or an organic phase, comprising:
   a) homogenising a sample comprising RNA and DNA in a mixture that comprises:
      i) an acidic denaturing composition comprising a chaotropic agent and phenol,
      ii) at least one cationic detergent, and
      iii) a water-insoluble organic solvent; and
   b) separating the phases of the mixture obtained in step a) to form a multi-phase mixture comprising an aqueous phase, optionally an interphase, and an organic phase, wherein the RNA is concentrated in said aqueous phase and DNA is concentrated in said organic phase and/or in said interphase.

19. The method of claim 18, wherein step a) comprises:
   (1) homogenising a sample comprising RNA and DNA in an acidic denaturing composition comprising a chaotropic agent and phenol, and
   (2) adding to the mixture obtained in step (1)
      i) at least one cationic detergent, and
      ii) a water-insoluble organic solvent.

* * * * *